(12) United States Patent
Dantus

(10) Patent No.: US 10,130,511 B2
(45) Date of Patent: Nov. 20, 2018

(54) ADAPTIVE LASER SYSTEM FOR OPHTHALMIC SURGERY

(71) Applicant: BOARD OF TRUSTEES OF MICHIGAN STATE UNIVERSITY, East Lansing, MI (US)

(72) Inventor: Marcos Dantus, Okemos, MI (US)

(73) Assignee: Board of Trustees of Michigan State University, East Lansing, MI (US)

(*) Notice: Subject to any disclaimer, the term of this patent is extended or adjusted under 35 U.S.C. 154(b) by 970 days.

(21) Appl. No.: 14/034,748

(22) Filed: Sep. 24, 2013

(65) Prior Publication Data

US 2014/0058367 A1 Feb. 27, 2014

Related U.S. Application Data

(63) Continuation of application No. PCT/US2012/030476, filed on Mar. 23, 2012.
(Continued)

(51) Int. Cl.
*A61B 18/20* (2006.01)
*A61F 9/008* (2006.01)
(Continued)

(52) U.S. Cl.
CPC ...... *A61F 9/00802* (2013.01); *A61F 9/00827* (2013.01); *A61F 9/00831* (2013.01); *A61F 9/00836* (2013.01); *H01S 3/005* (2013.01); *A61F 2009/0087* (2013.01); *A61F 2009/00846* (2013.01); *A61F 2009/00863* (2013.01); *A61F 2009/00872* (2013.01); *G02B 2207/114* (2013.01); *H01S 3/0092* (2013.01);
(Continued)

(58) Field of Classification Search
CPC .... A61F 9/00; A61F 9/00808; A61F 9/00804; A61F 9/00806; A61F 9/00821; A61F 9/00823; A61F 9/00825; A61F 9/00827; A61F 2009/00861; A61F 2009/00863; A61F 2009/00865; A61F 2009/0087; A61F 2009/00885; A61F 2009/00887
USPC .......................... 606/3–6, 10–12; 607/88, 89
See application file for complete search history.

(56) References Cited

U.S. PATENT DOCUMENTS 5,297,554 A 3/1994 Glynn et al.
5,432,569 A 7/1995 Ohtsuka
(Continued)

OTHER PUBLICATIONS

Lubatschowski, Holger; "Overview of Commerically Available Femtosecond Lasers in Refractive Surgery," Laser Zentrum Hannover e.V., 26 pages.
(Continued)

*Primary Examiner* — Ahmed Farah
(74) *Attorney, Agent, or Firm* — Harness, Dickey & Pierce PLC

(57) ABSTRACT

An adaptive laser system for ophthalmic use is provided. In another aspect, a relatively inexpensive laser is employed. In another aspect of the present system, non-linear optical imaging uses multiphoton fluorescences and/or second harmonic generation, to create three-dimensional mapping of a portion of the eye in combination with automated feedback to assist with a surgical operation. In a further aspect of the present system, the patient interface uses laser induced markings or indicia to aid in focusing and/or calibration. Still another aspect employs temporal focusing of the laser beam pulse.

66 Claims, 21 Drawing Sheets

Related U.S. Application Data

(60) Provisional application No. 61/467,737, filed on Mar. 25, 2011.

(51) Int. Cl.
*H01S 3/00* (2006.01)
*H01S 3/067* (2006.01)
*H01S 3/11* (2006.01)
*H01S 3/16* (2006.01)

(52) U.S. Cl.
CPC ......... *H01S 3/06733* (2013.01); *H01S 3/1112* (2013.01); *H01S 3/1618* (2013.01); *H01S 3/1675* (2013.01)

(56) References Cited

U.S. PATENT DOCUMENTS

| | | | |
|---|---|---|---|
| 5,561,678 A * | 10/1996 | Juhasz | A61F 9/008 372/12 |
| 5,673,097 A | 9/1997 | Heacock | |
| 5,993,438 A | 11/1999 | Juhasz et al. | |
| 6,099,522 A * | 8/2000 | Knopp | B23K 26/04 606/10 |
| 6,110,166 A | 8/2000 | Juhasz | |
| 6,648,877 B1 | 11/2003 | Juhasz et al. | |
| 6,706,036 B2 * | 3/2004 | Lai | B23K 26/0624 606/12 |
| 7,044,602 B2 | 5/2006 | Chernyak | |
| 7,113,327 B2 | 9/2006 | Gu et al. | |
| 7,131,968 B2 | 11/2006 | Bendett et al. | |
| 7,439,497 B2 | 10/2008 | Dantus et al. | |
| 7,450,618 B2 | 11/2008 | Dantus et al. | |
| 7,567,596 B2 * | 7/2009 | Dantus | G01J 11/00 250/281 |
| 7,583,710 B2 | 9/2009 | Dantus et al. | |
| 7,609,731 B2 | 10/2009 | Dantus et al. | |
| 7,655,002 B2 | 2/2010 | Myers | |
| 7,698,000 B2 | 4/2010 | Silberberg et al. | |
| 7,749,216 B2 | 7/2010 | Sumiya | |
| 7,973,936 B2 | 7/2011 | Dantus | |
| 8,185,209 B2 | 5/2012 | Dantus | |
| 8,208,504 B2 | 6/2012 | Dantus et al. | |
| 8,208,505 B2 | 6/2012 | Dantus et al. | |
| 8,265,110 B2 | 9/2012 | Dantus et al. | |
| 8,300,669 B2 | 10/2012 | Dantus et al. | |
| 8,311,069 B2 | 11/2012 | Dantus et al. | |
| 8,618,470 B2 | 12/2013 | Dantus et al. | |
| 8,630,322 B2 * | 1/2014 | Dantus | H01S 3/0057 372/24 |
| 8,633,437 B2 | 1/2014 | Dantus et al. | |
| 8,675,699 B2 | 3/2014 | Dantus et al. | |
| 2002/0095142 A1 * | 7/2002 | Ming | A61F 9/008 606/5 |
| 2006/0020259 A1 | 1/2006 | Baumeister et al. | |
| 2007/0123845 A1 * | 5/2007 | Lubatschowski | A61F 9/00825 606/5 |
| 2007/0282313 A1 | 12/2007 | Huang et al. | |
| 2008/0015662 A1 | 1/2008 | Tunnermann et al. | |
| 2008/0051769 A1 | 2/2008 | Mrochen et al. | |
| 2009/0122819 A1 | 5/2009 | Dantus et al. | |
| 2009/0131921 A1 * | 5/2009 | Kurtz | A61F 9/00825 606/4 |
| 2009/0137993 A1 | 5/2009 | Kurtz | |
| 2009/0149840 A1 | 6/2009 | Kurtz | |
| 2009/0188901 A1 | 7/2009 | Dantus | |
| 2009/0207869 A1 | 8/2009 | Dantus et al. | |
| 2009/0238222 A1 | 9/2009 | Dantus et al. | |
| 2009/0281530 A1 * | 11/2009 | Korn | A61F 9/008 606/5 |
| 2010/0082017 A1 | 4/2010 | Zickler et al. | |
| 2010/0123075 A1 | 5/2010 | Dantus et al. | |
| 2010/0137849 A1 * | 6/2010 | Hanft | A61F 9/00827 606/5 |
| 2010/0183634 A1 | 7/2010 | Luo et al. | |
| 2010/0187208 A1 | 7/2010 | Dantus et al. | |
| 2010/0191226 A1 | 7/2010 | Blumenkranz et al. | |
| 2010/0214534 A1 | 8/2010 | Kuebler et al. | |
| 2010/0292676 A1 * | 11/2010 | Larsen | A61F 9/008 606/4 |
| 2010/0324542 A1 | 12/2010 | Kurtz | |
| 2011/0028948 A1 | 2/2011 | Raksi et al. | |
| 2011/0028953 A1 * | 2/2011 | Raksi | A61F 9/008 606/4 |
| 2011/0211600 A1 | 9/2011 | Dantus et al. | |
| 2012/0076504 A1 | 3/2012 | Dantus et al. | |
| 2012/0147911 A1 | 6/2012 | Dantus et al. | |
| 2014/0321486 A1 | 10/2014 | Da Costa Ribeiro De Miranda et al. | |

OTHER PUBLICATIONS

Juhasz, Tibor, et al.; "Corneal Refractive Surgery with Femtosecond Lasers," IEEE Journal of Selective Topics in Quantum Electronics, vol. 5, No. 4, Jul./Aug. 1999, pp. 902-910.

Lubatschowski, Holger, et. al.; "Application of ultrashort laser pulses for intrastromal refractive surgery," Graefe's Arch Clin Exp Ophthalmol, 238, 2000, pp. 33-39.

Walmsley, Ian, et al.; "The role of dispersion in ultrafast optics," Review of Scientific Instruments, vol. 72, No. 1, Jan. 2001, pp. 1-29.

Thomas, Robert J., et al.; "A Comparative Study of Retinal Effects From Continuous Wave and Femtosecond Mode-Locked Lasers," Lasers in Surgery and Medicine, 31, 2002, pp. 9-17.

Cain, Clarence P., et al.; "Sub-50-fs laser retinal damage thresholds in primate eyes with group velocity dispersion, self-focusing and low-density plasmas," Graefe's Arch Clin Exp Ophthalmol, 243, 2005, pp. 101-112.

Vogel, A., et al., "Mechanisms of femtosecond laser nanosurgery of cells and tissues," Applied Physics B, 81, Nov. 15, 2005, pp. 1015-1047.

Zharov, V. P., et al.; "Microbubbles-overlapping mode for laser killing of cancer cells with absorbing nanoparticle clusters," Journal of Physics D: Applied Physics, 38, Jul. 22, 2005, pp. 2571-2581.

Ripken, T., et al.; "Comparison of various Femtosecond Lasers and Conventional Microkeratomes for Corneal Lamellar Cuts," presented at the 19th Congress of German Ophthalmic Surgeons, Nuremberg, Germany. May 25-28, 2006, pp. 1-4.

Letfullin, Renat R., et al.; "Laser-induced explosion of gold nanoparticles: potential role for nanophotothermolysis of cancer," Nanomedicine, 1(4), 2006, pp. 473-480.

Sun, Hui, et al.; "Femtosecond Laser Corneal Ablation Threshold: Dependence on Tissue Depth and Laser Pulse Width," Lasers in Surgery and Medicine, 39, 2007, pp. 654-658.

Wollenhaupt, Matthias, et al., "Femtosecond Laser Pulses: Linear Properties, Manipulation, Generation and Measurement," Springer Handbook of Lasers and Optics, Chapter 12, 2007, pp. 1-90.

Lubatschowski, Holger; "Laser Microtomy Opening a New Feasibility for Tissue Preparation," Optik & Photonik, No. 2, Jun. 2007, pp. 49-51.

"20/10 Perfect Vision AG Closes EUR 13.5 Million," NBGI Ventures, http://www.nbgiventures.com/news-article/items/Perfect_Vision.html, Oct. 2007, three pages.

Slade, Stephen G.; "How to Financially Justify the Femtosecond Laser," Cataract & Refractive Surgery Today Europe, Nov./Dec. 2007, pp. 58-60.

Coello, Yves, et al.; "Group-velocity dispersion measurements of water, seawater, and ocular components using multiphoton intrapulse interference phase scam," Applied Optics, vol. 46, No. 35, Dec. 10, 2007, pp. 8394-8401.

Dick, Manfred, et al.; Femtosecond Lenticule Extraction (FLEx) and Other Exciting Applications of Femtosecond Lasers—New Approaches to Cornea and Lens Laser Surgery, Wavefront Congress, 2008, 36 pages.

"Zapping with the light fantastic," The Economist, http://www.economist.com/node/10918079?story_id=10918079, Mar. 27, 2008, two pages.

"Carl Zeiss Meditec: First Femtosecond Eye-laser Installed in Asia," News & Infos, Optik & Photonik, No. 2, Jun. 2008, p. 4.

(56) References Cited

OTHER PUBLICATIONS

Binder, Perry S.; "Femtosecond Lasers," Cataract & Refractive Surgery Today, Oct. 2008, pp. 53-56.
"Surgical products, software enhancements and diagnostic platforms streamline efficiencies from the clinic to the operating room," Carl Zeiss Meditec, No. 242/08, Nov. 8, 2008, two pages.
Plamann, Karsten, et al.; "Ultrashort-pulse laser eye surgery uses fiber technology at 1.6 microns," SPIE, 2009, three pages.
Haimovitch, Larry; "Femtosecond Laser Technology May Mark a Quantum Leap," Irv Arons' Journal, Jun. 17, 2009, nine pages.
"Correlative Microscopy in Materials Analysis: Carl Zeiss Presents Solutions for Cross-Platform Microscopy," http://www.thefreelibrary.com/Correlative+Microscopy+in+Material+A . . . , Aug. 31, 2009, pp. 1-4.
Coughlan, Matthew A., et al.; "Parametric Spatio-Temporal Control of Focusing Laser Pulses," Optics Express, vol. 17, No. 18, Aug. 31, 2009, pp. 15808-15820.
"ESCRS 2009: The Next Wave in Cataract and Presbyopia Devices," Medical Devices Today, http://www.medicaldevicestoday.com/2009/11/escrs-2009-the-next-wave . . . , Nov. 19, 2009, three pages.
Kanellopoulos, Anastasios John, "Innovations in Femtosecond Laser Technology—The Use of the Wavelight® FS200 Laser for Flap Cutting during LASIK Surgery," European Ophthalmic Review, 2010, pp. 40-43.
Technolas Femtosecond Workstation 520F brochure, 2010, six pages.
Paulus, Yannis M., et al.; "Short-pulse Laser Treatment; Redefining Retinal Therapy," Retinal Physician, Jan./Feb. 2010, pp. 54-59.
Kessel, Line, et al.; "Non-Invasive Bleaching of the Human Lens by Femtosecond Laser Photolysis," PLos One, vol. 5, Issue 3, Mar. 2010, pp. 1-7.
Vyrghem, Jérôme C., et al.; "Efficacy, safety, and flap dimensions of a new femtosecond laser for laser in situ keratomileusis," J Cataract Refract Surg, vol. 36, Mar. 2010, pp. 442-448.
Yang, Xiaobo, et al.,; "Accidental Macular Injury from Prolonged Viewing of a Plasma Flash Produced by a Femtosecond Laser," American Academy of Ophthalmology, Mar. 3, 2010, pp. 972-975.
"OptiMedica Unveils Details Behind Femtosecond Laser for Cataract," http://www.medicalnewstoday.com/printerfriendlynews.php?newsid=185106, Apr. 12, 2010, two pages.
Aptel, Florent, et al.; "Multimodal Nonlinear Imaging of the Human Cornea," Investigative Ophthalmology & Visual Science, vol. 51, No. 5, May 2010, pp. 2459-2465.
Voronin, A. A., et al.; "Ionization penalty in nonlinear optical bioimaging," Phsyical Review E, 81, May 17, 2010, pp. 051918-1-051918-7.
"Optical Express Invests $12 Million to Enhance Patient Care," http://uk.opticalexpress.com, Jun. 9, 2010, one page.
Plamann, K., et al.; "Ultrashort pulse laser surgery of the cornea and the sclera," IOPscience, J. Opt. 12 084002, Jul. 15, 2010, pp. 1-30.

Vitek, Dawn N., et al.; "Temporally focused femtosecond laser pulses for low numerical aperture micromaching through optically transparent materials," Optics Express, vol. 18, No. 17, Aug. 16, 2010, pp. 18086-18094.
Straub, Laura, "New Generation of Femtosecond Lasers Emerges," Cataract & Refractive Surgery Today Europe, Sep. 2010, nine pages.
Bonanni, Brian A.; "Z-LASIK The Latest Technique in Laser Vision Correction," www.aesthetictrends.com, Sep./Oct. 2010, pp. 1-4.
"Technolas Perfect Vision unveils two new pioneering laser procedure innovations at the XXVIII Congress of the ESCRS, Paris," press release, Sep. 3, 2010, two pages.
"Femtosecond laser technology moving quickly to improve LASIK results," OSNSuperSite, http://www.osnsupersite.com/print/.aspx?rid=68363, printed Nov. 13, 2010, one page.
"Laboratory of Developmental and Regenerative Biology of Neural Circuits," Chang Lab Research, Cincinnati Children's Hospital Medical Center, http://cincinnatichildrens.org/research/div/dev-biologyffac-labs/ch . . . , printed Nov. 13, 2010, three pages.
Palczewska, Grazyna, et al.; "Noninvasive multiphoton fluorescence microscopy resolves retinol and retinal condensation products in mouse eyes," Nature Medicine, vol. 16, No. 12, Dec. 2010, pp. 1444-1450.
Fontevecchia, Agustino; "Novartis is Eye-Care King After Acquiring Alcon," http://wwwforbes.com/2010/12/15/novarits-alcon-pfizer-markets-equitie . . . , Dec. 15, 2010, three pages.
Tu, Haohua, et al.; "Scalar generalized nonlinear Schrödinger equation-quantified continuum generation in an all-normal dispersion photonic crystal fiber for broadband coherent optical sources," Optics Express, vol. 18, No. 26, Dec. 20, 2010, pp. 27872-27884.
Tu, Haohua,, et al.; "Cross-validation of theoretically quantified fiber continuum generation and absolute pulse measurement by MIIPS for a broadband coherently controlled optical source," Optical Society of America, 2011, six pages.
"Different Concepts to Approach the Same Technology," Expert Rev Ophthalmol., 2011; 6(1), one page.
Nie, Bai, et al.; "Sub-45 fs 20 nJ per pulse all-normal-dispersion fiber laser characterization and compression," Optical Society of America, 2011, six pages.
"Femtosecond laser system approach promising for cataract surgery," http://online.qmags.com/BOW0111/printpage.aspx?pg=12&pm=0, printed Feb. 16, 2011, one page.
Reggiani-Mello, Glauco, et al.; "Comparison of Commercially Available Femtosecond Lasers in Refractive Surgery," Expert Rev Ophthalmol., 6(1), Mar. 1, 2011, pp. 55-65.
"Guidebook for Laser Eye Surgery Should I Choose Femtosecond Intra-Lasik & traditional Lasik?" Lasik Reviews.co.uk, http://www.lasikreviews.co.uk/laser-vision-correction-intralasik-lasik.htm, printed Mar. 24, 2011, two pages.

* cited by examiner

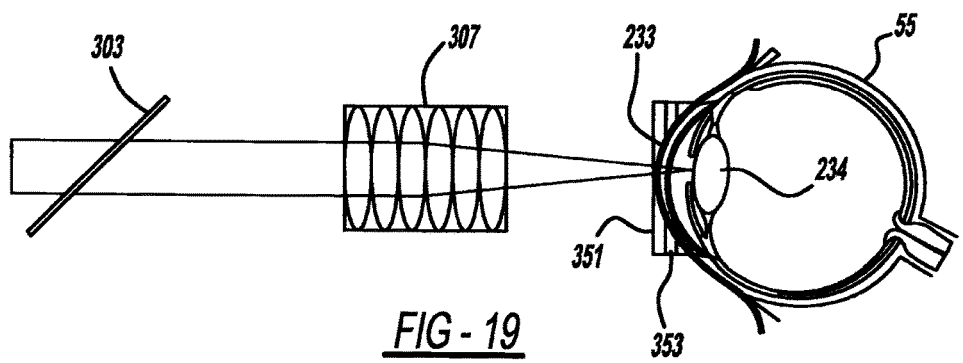
FIG - 19
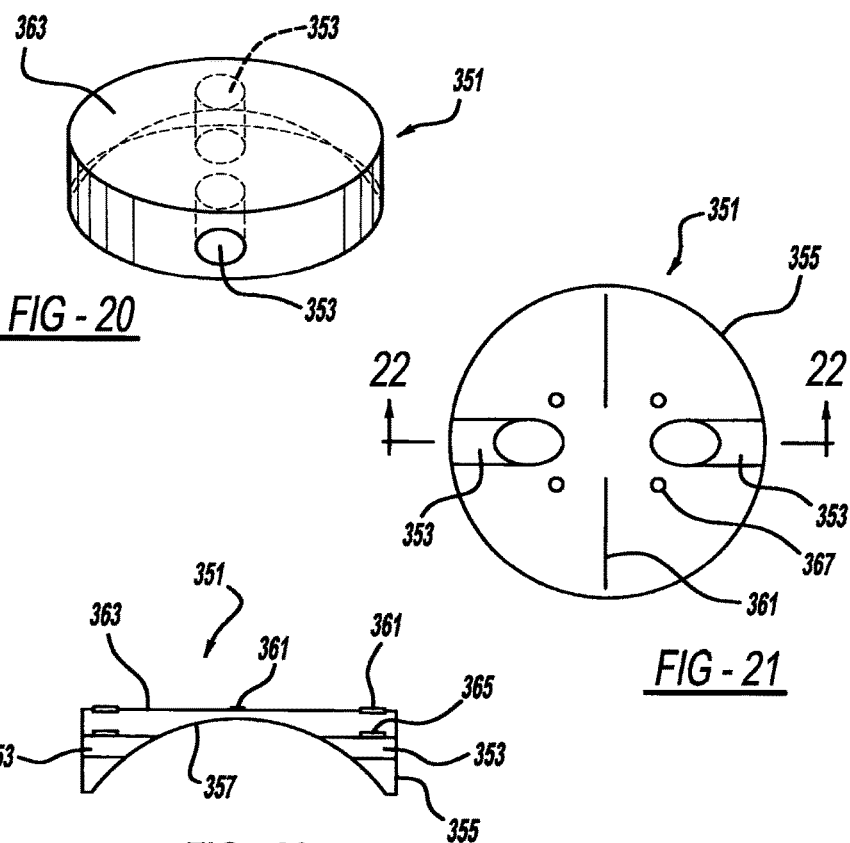
FIG - 20
FIG - 21
FIG - 22

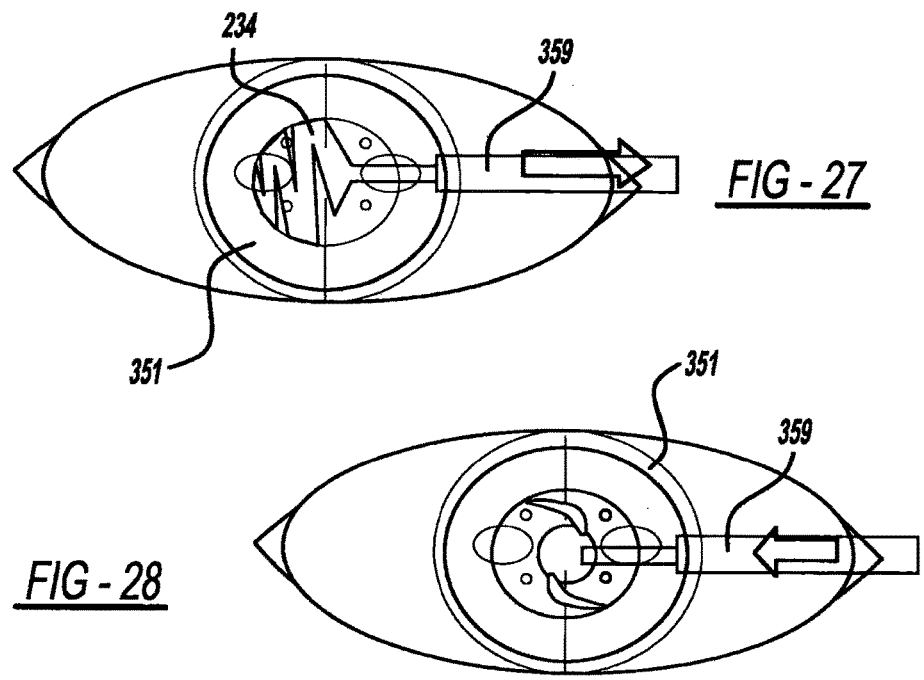
FIG - 27
FIG - 28
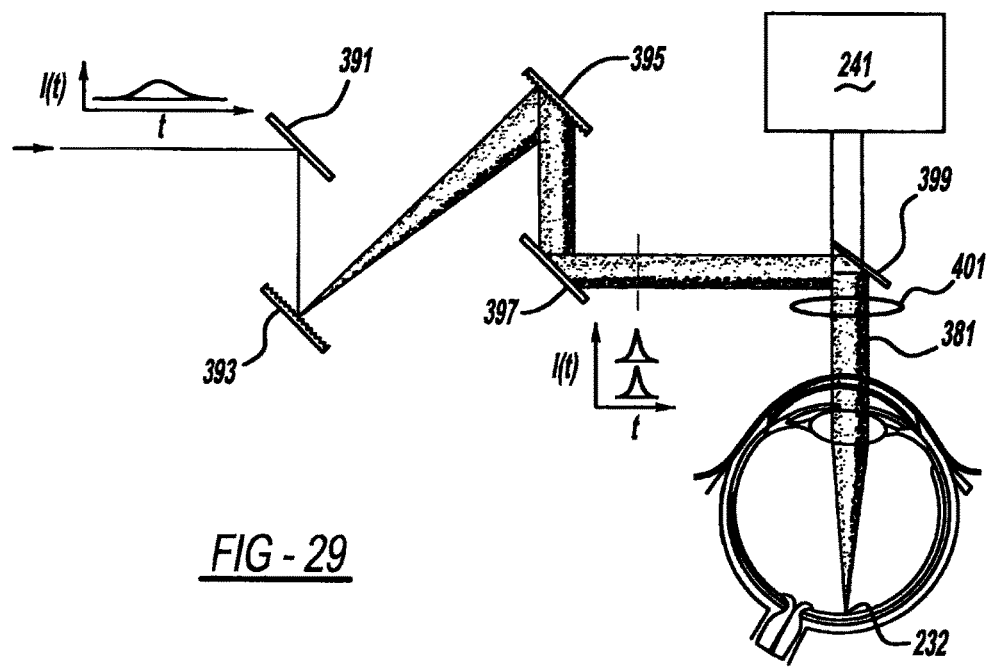
FIG - 29

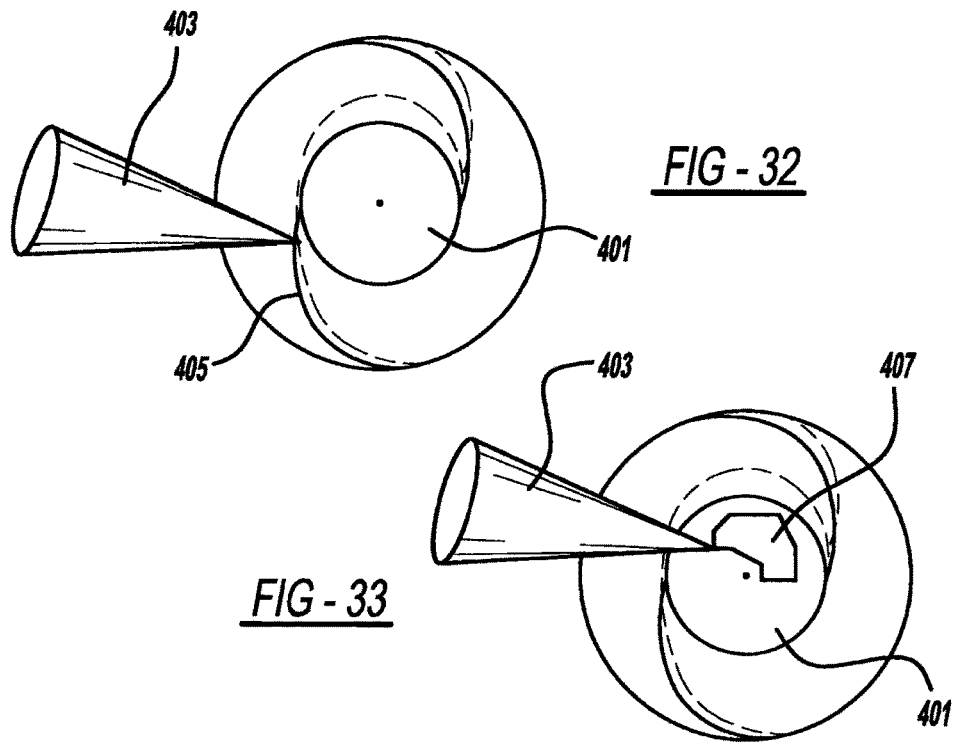
FIG - 32
FIG - 33
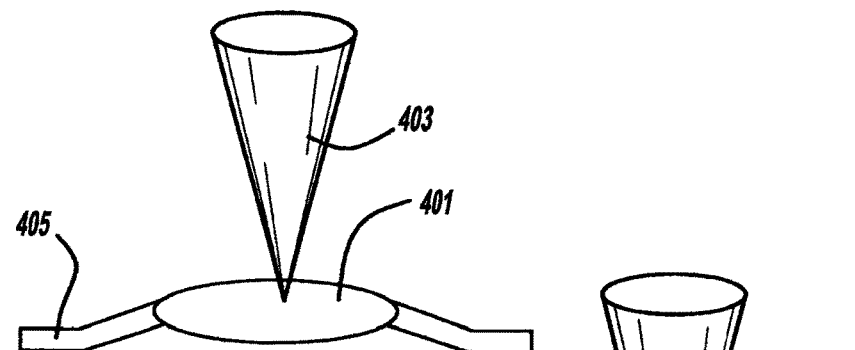
FIG - 34
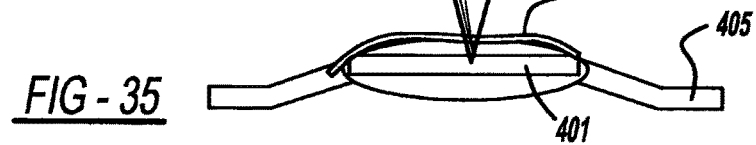
FIG - 35

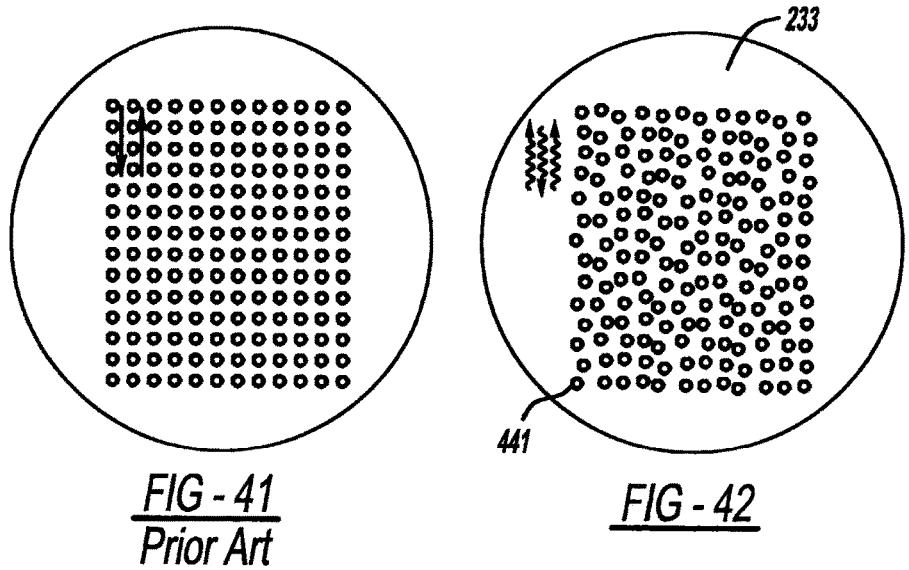
FIG - 41
Prior Art
FIG - 42
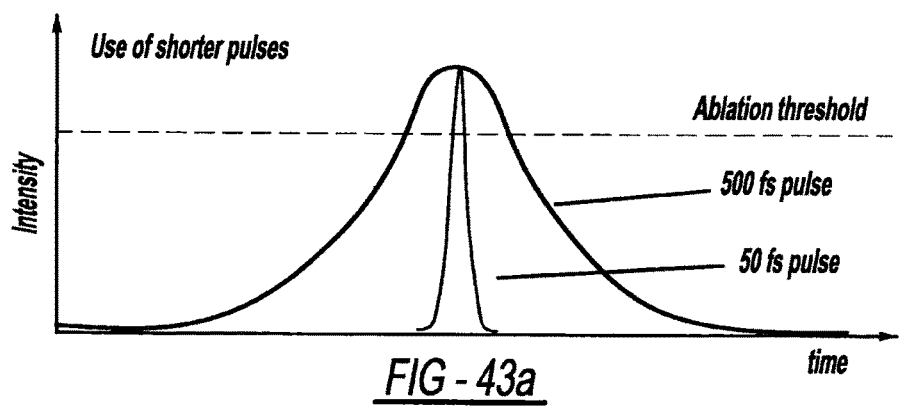
FIG - 43a
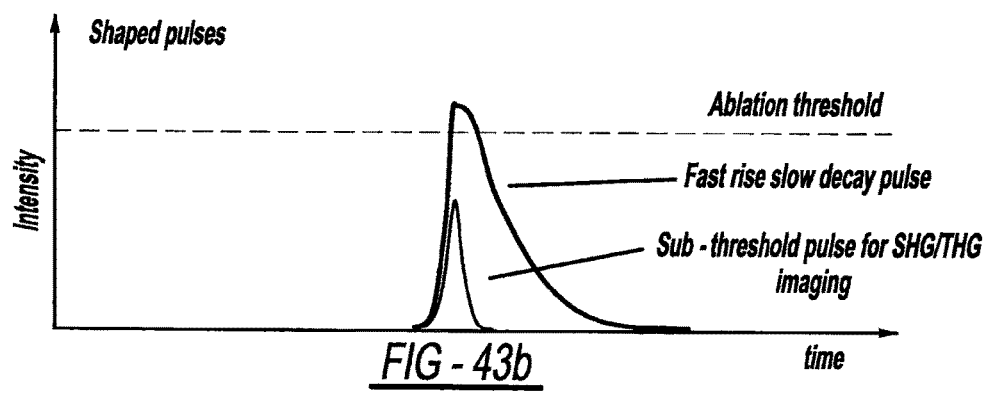
FIG - 43b

ADAPTIVE LASER SYSTEM FOR OPHTHALMIC SURGERY

CROSS-REFERENCE TO RELATED APPLICATIONS

This application is a continuation application of PCT International Patent Application Serial No. PCT/US2012/030476, filed on Mar. 23, 2012, which claims priority to U.S. Provisional Application Ser. No. 61/467,737, filed on Mar. 25, 2011, both of which are incorporated by reference herein.

BACKGROUND AND SUMMARY

The present invention relates generally to laser systems and more particularly to an adaptive laser system for ophthalmic use.

It has become common to employ lasers for eye surgery, including cataract surgery, refractive surgery, glaucoma surgery, corneal grafting retinal treatments, keratoplasty, and the like. More recently, ultrafast lasers, having an amplified output of at least 1 µJ per pulse and a duration of at least 250 fs have been used. "Aside from the technical benefits that come along with femtosecond lasers, there were new side effects that arose with the technology that are now better understood. The formation of a bubble layer occurs along the cutting plane, which in some cases leads to an escape of some bubbles into deeper stroma with the formation of an OBL [opaque bubble layer] . . . . These deeper bubbles may take a few hours to disappear, and if severe, may impair the aim of the eye tracker during surgery." G. Reggiani-Mello, et al., *Comparison of Commercially Available Femtosecond Lasers in Refractive Surgery*, Expert Rev. Ophthalmol., 6 (1): 55-65 (Mar. 1, 2011). It is also problematic that bubbles can cause undesired tears in the cornea during surgery. Furthermore, K. Plamann, et al., *Ultrashort Pulse Laser Surgery of the Cornea and the Sclera*, J. Opt. 12, 084002 (Jul. 15, 2010), states that such bubbles are created due to nonlinear laser-tissue interaction processes caused by these femtosecond pulse lasers.

Additional challenges of femtosecond pulses are presented in paragraph numbers [0041]-[0054] of U.S. Patent Publication No. 2011/0028948 entitled "Optical System for Ophthalmic Surgical Laser" which published on Feb. 3, 2011, and is incorporated by reference herein. Additional ophthalmic procedures using lasers are disclosed in U.S. Patent Publication No. 2010/0324542 entitled "Method to Guide a Cataract Procedure by Corneal Imaging" which published on Dec. 23, 2010, U.S. Patent Publication No. 2010/0082017 entitled "Laser Modification of Intraocular Lens" which published on Apr. 1, 2010, and U.S. Pat. No. 7,131,968 entitled "Apparatus and Method for Opthalmologic Surgical Procedures Using a Femtosecond Fiber Laser" which issued on Nov. 7, 2006; all of which are incorporated by reference herein. It is noteworthy, however, that femtosecond lasers employed with conventional ophthalmic systems are extremely expensive and subject to mechanical failure related to the water cooling system, optical including damage to the SESAM saturable absorber, and electronics, if not regularly maintained which leads to significant lost opportunity costs and delays in surgical procedures when the lasers are being fixed.

In accordance with the present invention, an adaptive laser system for ophthalmic use is provided. In another aspect, a compact and relatively inexpensive laser is employed, with a direct diode pumped or Yb-doped gain element, in either a fiber or free space type configuration, without amplification, which emits a laser beam pulse having a duration less than 100 fs and an output energy less than 2 µJ per pulse. In yet another aspect, a titanium sapphire oscillator emits a laser beam pulse having a duration less than 30 fs and output energy less than 30 nJ per pulse. This low cost approach is advantageous for use in a multiple laser construction where two or more lasers can be arranged on the same machine and selected based on the type of surgical operation being performed, and/or used in a modularized manner as an instant replacement in the event that one laser fails.

In another aspect of the present system, non-linear optical ("NLO") imaging uses multiphoton fluorescences and/or second and/or third harmonic generation, to create three-dimensional mapping of a portion of the eye in combination with automated feedback to assist with a surgical operation. This can advantageously replace optical coherence tomography ("OCT") for determining the precise position of tissues and tracking performance of the system. In a further aspect of the present system, the patient interface uses laser induced markings or indicia to aid in focusing and/or calibration. Still another aspect employs temporal focusing of the laser beam pulse having a shorter than 100 fs duration. This advantageously assists in accurately controlling a depth of cut by a laser beam pulse without harming adjacent tissue. Temporal focusing is ideally suited for ultrafast laser pulses of less than 50 fs. A further aspect employs temporal focusing for diagnoses and/or treatment of retinal disease.

Moreover, automatic characterization and adaptive correction of non-linear optical distortions in a laser beam used for ophthalmic surgical procedures, which include spectral phase dispersion caused by the laser source, optics and the eye being treated as well as spatial distortion caused primarily by the eye being treated, are provided in an aspect of the present system. The adaptive control over the laser pulses gives the versatility of the system to, for example, ablate, cut, bleach, correct, modify, and non-invasively image ophthalmic tissues or an intraocular lens with the same unit regardless of their depth inside the eye. Another aspect employs a laser to make a generally accordion-like or other contiguous pattern cut on a diseased lens so that the lens can be removed as a single piece from the eye and thereafter replaced by an intraocular lens. A method of use and/or of manufacturing any of the preceding aspects is also provided.

The interest in using shorter pulses, despite the fact that they are more prone to dispersion, is the overall reduction in the amount of energy per pulse required to cause a modification or cut in the tissue for a particular surgical procedure. The present system uses laser pulses that are ten or more times shorter in duration than those conventionally used. The shorter pulses result in a ten-time reduction of average laser intensity used on the eye, making every procedure safer. This advantage is consistent with R. J. Thomas et al., *A Comparative Study of Retinal Effects from Continuous Wave and Femtosecond Mode-Locked Lasers*, Lasers in Surgery and Medicine 31, 9-17 (2002) who generally determined that damage to the retina can be directly related to the average intensity of the laser.

The present laser system is advantageous over conventional devices in that the present system should reduce, if not eliminate, undesired bubbles created during ophthalmic surgery when used with the characterization and correction control aspect. The considerably shorter pulses being considered in the present system have a pulse duration that is below that required for the creation of avalanche ionization, thereby reducing the possibility of forming necrotic tissue and reducing, if not preventing bubble formation. The elimination of bubbles would eliminate the conventional need to create a capsulotomy, which is used to allow the bubbles accumulated during the lens ablation. The capsulotomy procedure is not presently covered by U.S. health insurance. Phaco removal is presently the procedure that takes the longest. If the capsulotomy is not required and the laser operates at a much faster repetition rate, the present invention results in faster procedures. The specific femtosecond laser configuration of another aspect of the present system advantageously provides a considerably less expensive laser system than traditional femtosecond laser devices. This should increase the availability of these types of systems for surgical procedures in rural areas and less prosperous countries, and allowing for modularized backup lasers which also avoid down time during shipping and repair of a broken traditional laser. Additional advantages and features of the present invention will become apparent from the following description and appended claims, taken in conjunction with the accompanying drawings.

BRIEF DESCRIPTION OF DRAWINGS

FIG. 19 is a diagrammatic representation showing a variation of an NLO compatible patient interface used with the laser system;

FIG. 20 is a perspective view showing the NLO compatible patient interface of FIG. 19 used with the laser system;

FIG. 21 is a true elevational view showing the NLO patient interface of FIG. 19 used with the laser system;

FIG. 22 is a cross sectional view, taken along line 22-22 of FIG. 21, showing the NLO patient interface used with the laser system;

FIG. 27 is a diagrammatic representation showing one-piece lens removal used with another variation of the laser system;

FIG. 28 is a diagrammatic representation showing introduction of an intraocular lens used with the laser system;

FIG. 29 is a diagrammatic representation showing temporal focusing for retinal surgical treatments used with the laser system;

FIGS. 32-33 are true views showing the laser system using non-invasive adjustment of the position and the refractive properties of an intraocular lens following a cataracts lens replacement;

FIGS. 34 and 35 are diagrammatic side views showing non-invasive adjustment of intraocular lens refraction used with the laser system;

FIG. 41 is a true elevational view showing a prior art flap cutting pattern;

FIG. 42 is a diagrammatic true view showing an oscillating flap cutting pattern used with the laser system;

FIGS. 43a and b are graphs showing temporal shaping for improved ablation used with the laser system;

DETAILED DESCRIPTION

Figure 1:
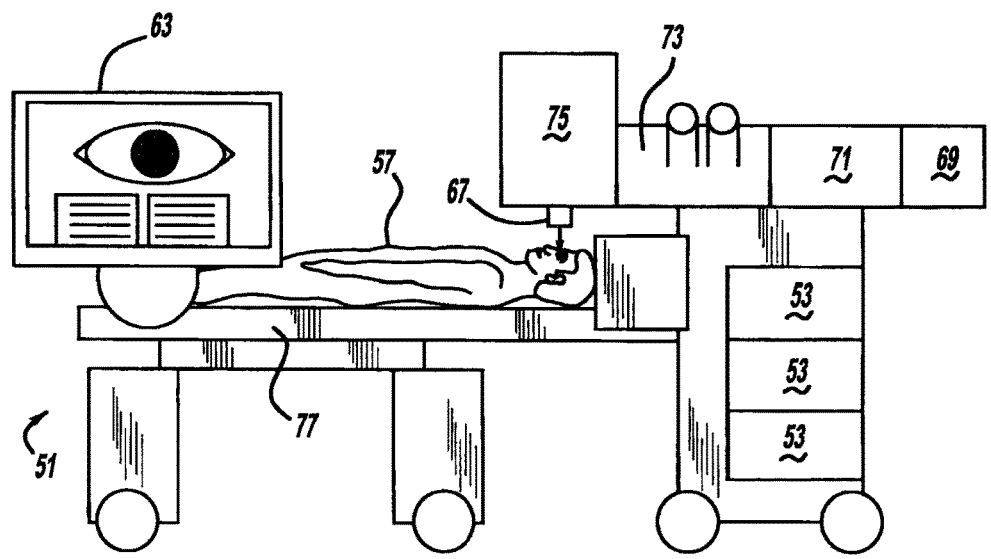
FIG. 1 is a schematic representation showing the laser system.

Referring to FIG. 1-4, the preferred embodiment of an adaptive laser system or machine unit 51 for ophthalmic use of the present invention uses one or more ultrafast lasers 53 to operate on an eye 55 of a patient 57. Each laser 53 is preferably configured with a solid state, unamplified and air cooled diode-pumped Yb gain, in a fiber or hybrid free-space-fiber. The large bandwidth of the preferred laser arises through self-phase modulation within the cavity fiber or through pumping a photonic crystal fiber. This provides a relatively inexpensive laser assembly ideally suited for modularized and interchangeable use. The laser preferably emits a pulse intensity less than 5 µJ and a duration less than 150 fs, more preferably less than 100 fs, and even more preferably less than 50 fs, and for some uses less than 10 fs. The repetition rate is greater than one million pulses per second. This allows faster procedures. Similarly, it is desirable to reduce the energy per pulse to levels below 100 nJ and preferably below 10 nJ. The repetition rate of the laser is higher than 200 kHz, and preferably greater than 1 MHz. In one example, the duration is less than 80 fs, the output is less than 0.5 µJ, and the repetition rate is greater than 5 MHz. A faster repetition rate with lower energy pulses reduces the 'bridges' formed between ablated tissue and achieves a smoother cut. Conventional systems have a pulse-to-pulse ablation depth variation of 20 µm, but with the faster repetition rate and lower energy, shorter pulses of the present system it is estimated that the point-to-point variation in the ablated tissue will improve by as much as an order of magnitude.

This laser system 51, optionally and preferably, employs an automated multiphoton intrapulse interference phase scan unit 69 (MIIPS®) which includes programmed software instructions for automatically measuring/characterizing and/or compensating/correcting non-linear optical phase distortions in the laser beam pulses in less than five minutes, and more preferably less than five seconds. The software is stored in non-transient RAM, ROM, removable disc or memory stick, which is run by one or more microprocessors in a computer controller 63. The details of the MIIPS® software and procedures are disclosed in the following U.S. Patent Publications and Patents: 2010/0187208 entitled "Laser Pulse Synthesis System" which published on Jul. 29, 2010; 2009/0257464 entitled "Control System and Apparatus for Use with Ultra-Fast Laser" which published on Oct. 15, 2009; 2009/0238222 entitled "Laser System Employing Harmonic Generation" which published on Sep. 24, 2009; 2009/0122819 entitled "Laser Pulse Shaping System" which published on May 14, 2009; U.S. Pat. No. 7,609,731 entitled "Laser System Using Ultra-Short Laser Pulses" which issued on Oct. 27, 2009; U.S. Pat. No. 7,567,596 entitled "Control System and Apparatus for Use With Ultra-Fast Laser" which issued on Jul. 28, 2009; and U.S. Pat. No. 7,450,618 entitled "Laser System Using Ultrashort Laser Pulses" which issued on Nov. 11, 2008. All of these patents and patent publications are incorporated by reference herein. Furthermore, additional aspects of the MIIPS® procedures used to measure a chromatic dispersion of an ocular component with regard to seawater are discussed in M. Dantus, *Group-Velocity Dispersion Measurements of Water, Seawater and Ocular Components Using Multiphoton Intrapulse Interference Phase Scan,"* Applied Optics, Vol. 46, No. 35, pp. 8394-8401 (Dec. 10, 2007).

The preferred laser system combines fiber and free space elements to generate a bandwidth greater than 60 nm. Furthermore, nonlinear polarization provides mode locking. An intracavity spectral filter is used. Additionally, a compact free space oscillator produces pulses longer than 100 fs followed by a fiber, wherein self-phase modulations cause sufficient bandwidth to permit compression of the pulses to durations shorter than 50 fs. Optionally, the pulse shaper can cause each pulse to separate into a train of at least two pulses. Moreover, an objective lens has an aperture that can be used to limit a numerical aperture, and hence, the length over which the laser alters the target tissue; this is ideally suited for penetrating lamellar keratoplasty, endothelial keratoplasty, tunnel cutting, and cutting and extraction of a nucleus.

Figure 2:
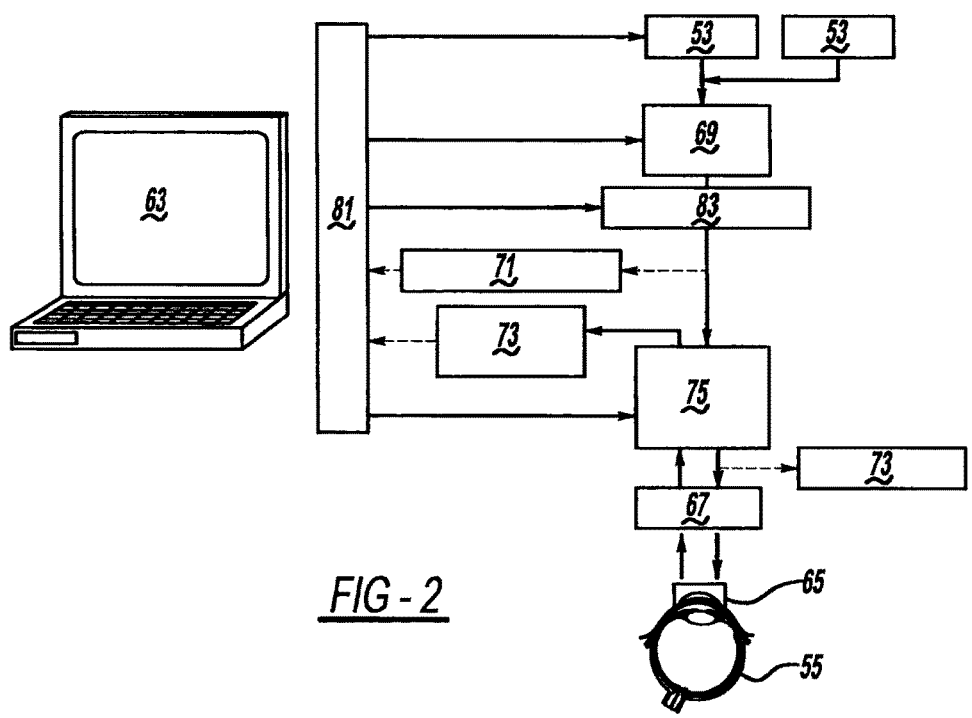
FIG. 2 is a schematic representation showing how different components of the laser system interact.

FIGS. 1 and 2 show a modular design that incorporates two or three lasers 53 that can be used alternatively or in tandem. Even total failure of one laser allows the instrument to continue normal operation. System 51 uses nonlinear optical imaging instead of OCT for three-dimensional mapping and xyz calibration. A disposable patient interface 65 is employed that has especially bright NLO markings that the system can use for xyz calibration and to test ablation. An instrument housing, containing a microscope objective, lens and/or other optics 67 through which the laser beam pulses transmit, is positioned adjacent to or against interface 65. System 51 also uses temporal (or more accurately spectral) focusing to permit greater depth control when high-numerical aperture ("NA") objectives cannot be used for very long working distances. These features will be discussed in more detail hereinafter.

Ophthalmic surgical machine unit 51 further includes a temporal pulse shaper 69, a beam diagnostics unit 71, an NLO imaging unit 73, and XYZ scanning and temporal focusing optics 75. Computer controller 63 includes an input keyboard and an output doctor interface screen. Patient 57 is placed prone on a supporting bed 77 with positioning adjustment. The low cost modular laser system provides the source of ultrashort pulses required for performing multiple different surgical and related treatment procedures. The laser output is conditioned by the temporal shaping unit. A portion of the main beam transmits to beam diagnostic unit 71 where the controller uses the software instructions to automatically determine the required pre-compensation to ensure optimum laser performance at the focal plane; this may optionally include the MIIPS® software. During the procedures, the system is capable of forming photographic as well as NLO images of the eye for the purposes of calibration, for making a three dimensional map of the eye, for tracking eye motion and for planning different procedures. The imaging components and detectors are located in multi-modal NLO imaging unit 73. Under the direction of the controller-based software, the laser beam is automatically scanned and the focal plane moved to achieve full xyz positioning, by the use of galvonometer 400 controlled mirrors in beam-scanning unit 75. For all procedures in the proximal region of the eye, high numerical aperture objective 67 is used to focus the beam. The surgeon directs and monitors the planned treatment via the interactive computer display screen 63. A computer interface bus 81, and on/off and intensity controlling circuits 83 are also provided.

Figure 3:
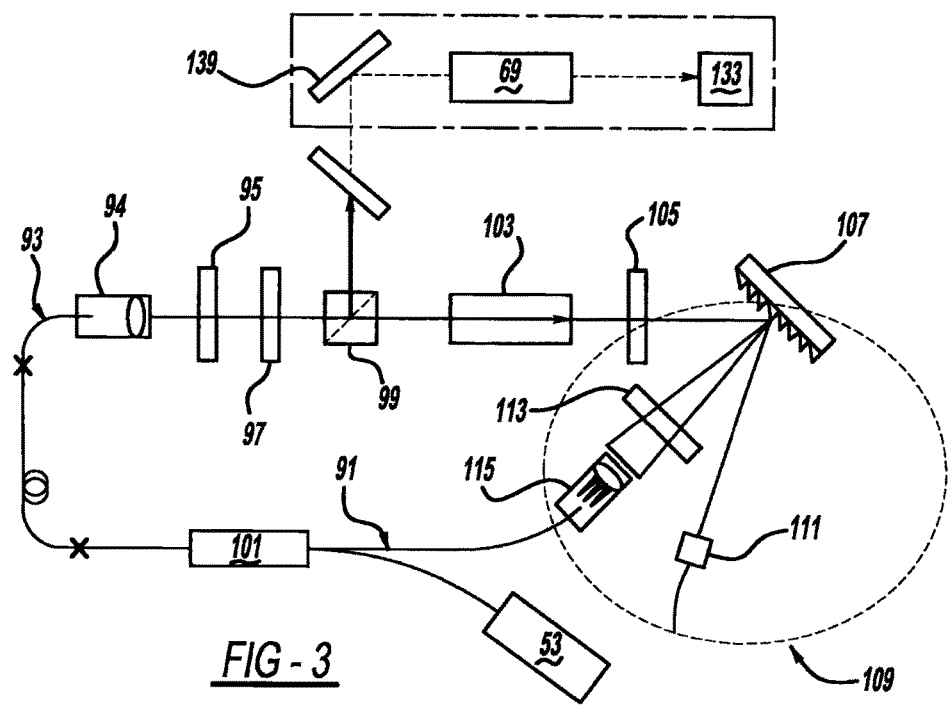
FIG. 3 is a schematic representation showing a high power, femtosecond fiber oscillator used with the laser system.

FIG. 3 shows double-clad Yb, all-normal-dispersion fiber laser 53. This system includes single mode fiber sections 91 and 93, a collimator 94, quarter 95 and half 97 waveplates, and a polarizing beam splitter 99, the ends of the 2.5 m Yb doped double-clad gain fiber (for example, Coractive DCF-YB-10/128) are spliced to fiber sections 91 and 93, respectively, and a fiber combiner 101 is employed. The gain fiber is pumped by a CW diode laser 53 at 976 nm (for example, LIMO), with a range of pump power from 10 to 30 watts. The other section 93 of the single mode passive fiber which follows the gain fiber is approximately 0.35 m long. Polarizing beam splitter 99, an isolator 103, and waveplates (half- and quarter-waveplates 97 and 95 on the left side, and a quarter-waveplate 105 on the right side, as illustrated) act as an artificial saturable absorber, due to the nonlinear polarization evolution of the laser pulses through the fiber. By adjusting these waveplates, passive mode-locking can be achieved. The half-waveplate preceding a grating 107, with an intracavity spectral filter 109, helps to maximize the efficiency of the grating first order diffraction. The zeroth order diffraction can be detected by a photodiode 111 and sent to an oscilloscope and radio frequency spectrum analyzer. Each laser module is protected by a Faraday rotator that prevents back-scattered laser light from entering the laser output. Another quarter-waveplate 113 and collimator 115 are downstream of grating 107 control the bandwidth and polarization of pulses before entering gain fiber 101. It is desirable that the input to the gain fiber has circular or elliptical polarization for mode locking.

One version of a compact sub-45 fs fiber laser oscillator is capable of producing 20 nJ. Higher output power, up to 100 nJ can be obtained by using large mode area fibers including chirally-coupled core with a diameter up to 100 microns. This laser 53 differs from prior lasers as follows. The preferred present lasers 53 have a greater than 20% wall plug electrical efficiency, cost savings are achieved from no replacement of flash lamps, the mean time between failure is between 1 and 10 years of continuous use, and warm up is essentially instantaneous unlike prior lasers which require warm up times of at least 30 minutes. Furthermore, the present system advantageously achieves a fixed spot size and spot profile at all power levels, maintenance-free or low maintenance operation, minimal spare parts, and it is air-cooled or has minimal cooling requirements, the present laser has a smaller size, and it has no requirement for alignment. Moreover, the down-time caused by conventional devices is eliminated by having an instant-on, replacement laser of the present system. Additionally, the modular laser of the present system can be shipped for service since the modular design makes it very simple to remove and replace the laser by minimally skilled technician. Fiber lasers guarantee alignment when the module is re-inserted. The modular and low cost configuration allows a medical technician (who is not a laser expert) to replace the laser in less than one hour and more preferably less than five minutes.

Figure 4:
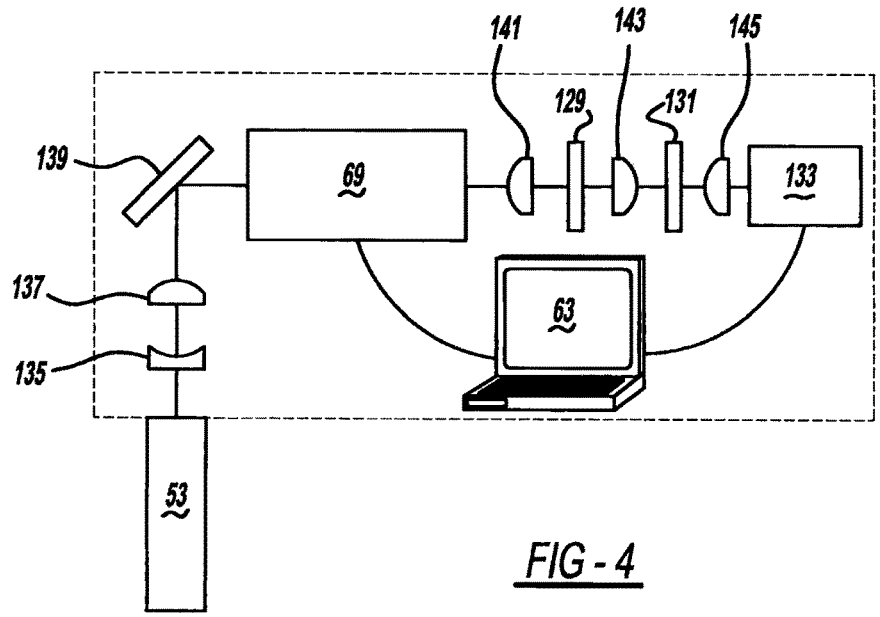
FIG. 4 is a schematic representation showing a multiphoton intrapulse interference phase scan unit used with the laser system.

As can be observed in FIG. 4, compression of the fiber laser output and the pre-compression of the objective and other optics is carried out by pulse shaper 69. Here a 4f shaper uses the MIIPS® software and procedures. A beta-barium borate SHG crystal 129 is used to generate SHG. Furthermore, a short pass IR optical filter 131 is used to transmit the SHG which is then dispersed with a compact spectrometer 133 having a CCD detector and connected to computer controller 63. A preferred embodiment of the 4f shaper is the FemtoFit™ pulse shaper and MIIPS® unit from Biophotonic Solutions Inc. Additional optics are used, such as telescope lenses 135 and 137, a reflective mirror 139, and other lenses 141, 143 and 145. It may be only necessary to conduct the MIIPS® operation once per day, to measure and correct for dispersion, including high order terms, in the pulses. Dispersion correction is especially desirable when the laser operates at depths greater than one millimeter from the surface of the eye.

Figure 5:
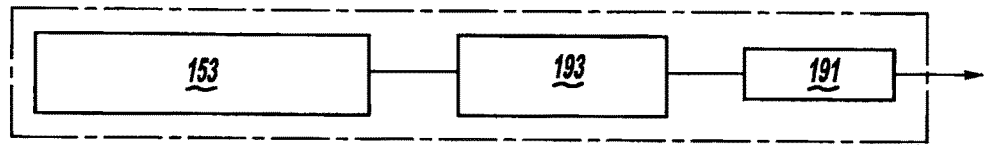
FIGS. 5 and 6 are schematic representations showing a high power, hybrid femtosecond fiber oscillator used with an alternate embodiment of the laser system.
Figure 6:
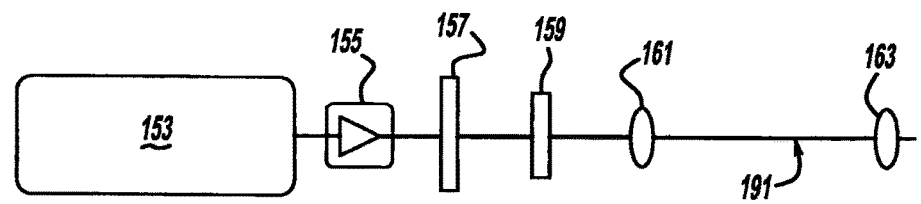

FIGS. 5 and 6 illustrate an alternative to the ultrashort pulse high energy fiber laser by use of a hybrid fs fiber oscillator laser 153. In this case, the high power oscillator is a free space, diode pumped and solid-state Yb:KYW laser, capable of producing 500 nJ of energy per pulse, with each pulse having a duration of 200 fs. The output is then coupled into a PCF fiber 191 of approximate length 1-100 cm, by a coupling module 193. The pulse gains bandwidth through self phase modulation, also known as supercontinuum generation. The output of this source is then compressed to produce pulses as short as 9 fs in duration with an average output power of 360 mW. An isolator 155, attenuator 157, a half-wave plate 159, a focusing lens 161 and a collimating lens 163 are also used.

Figure 7:
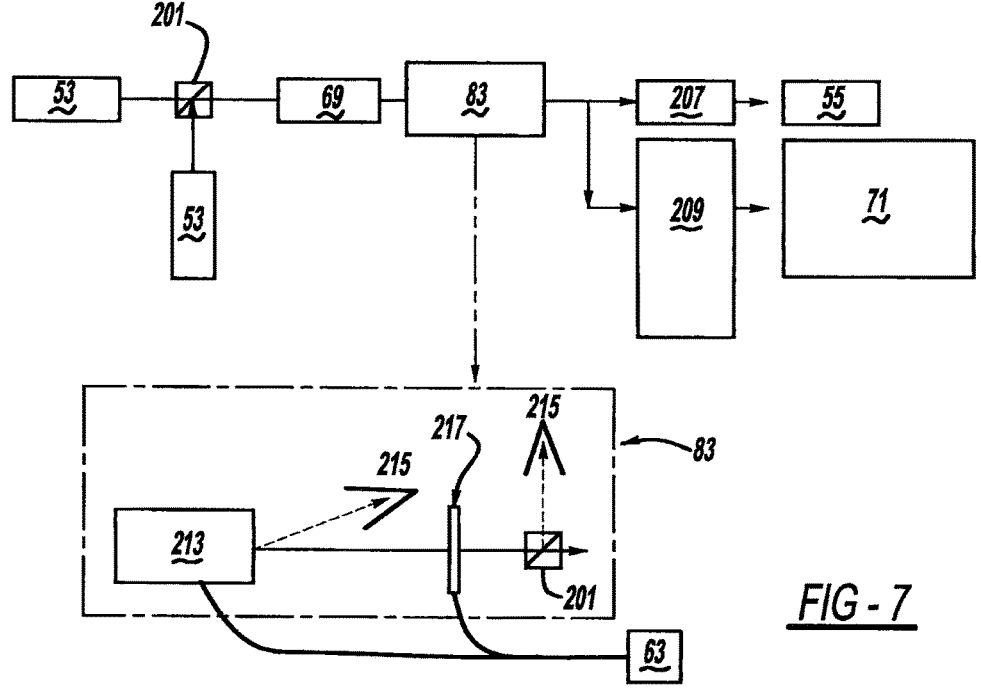
FIG. 7 is a schematic representation showing a modularized femtosecond fiber oscillator embodiment used with the laser system.

Reference should now be made to FIG. 7. One or more spare femtosecond lasers 53 are mounted to the machine unit and can almost immediately be used for replacement by the simple automatic controller or manual user actuation of a switch. The modular laser systems can run at the same time to speed up procedures or can be kept in the stand-by setting until needed. The energy consumption of each laser is extremely low compared to traditional femtosecond sources used in ophthalmology so the present system can optionally, alternate lasers to make sure one or more are ready at all times. Each laser 53 advantageously costs approximately one third of traditional femtosecond laser systems which allow the present modular design to be cost effective. The reduced requirement for maintenance and the cost of immediate service warranty further helps the affordability of the proposed modular design. The design of a system with three such lasers is envisioned where if one laser fails, it can be removed in less than five minutes and sent for repairs, leaving the entire ophthalmic unit with one or more spare lasers while the failed module is being repaired or replaced. In this configuration, the modularized system includes a polarizing cube beam combiner 201, a shaper 69, an on/off and intensity circuit 83, mirror and lens optics 207, optional simulation optics module 209 to simulate desired focal depth, and beam diagnostics 71 for focusing on an SHG crystal and obtaining an SHG spectrum. The lasers are always used at optimum intensity. On/off and intensity control 83 for each individual procedure is regulated by a combination of an acousto-optic modulator 213 and a combination of a half-wavelength plate 217 and a polarizer. The acousto-optic modulator diffracts part of the beam or picks individual pulses to control the effective repetition rate of the laser. The half-wavelength plate rotates the polarization of the laser such that only the correct polarization makes it through the polarizing cube and the wrong polarization is sent to a beam dump 215.

Figure 8:
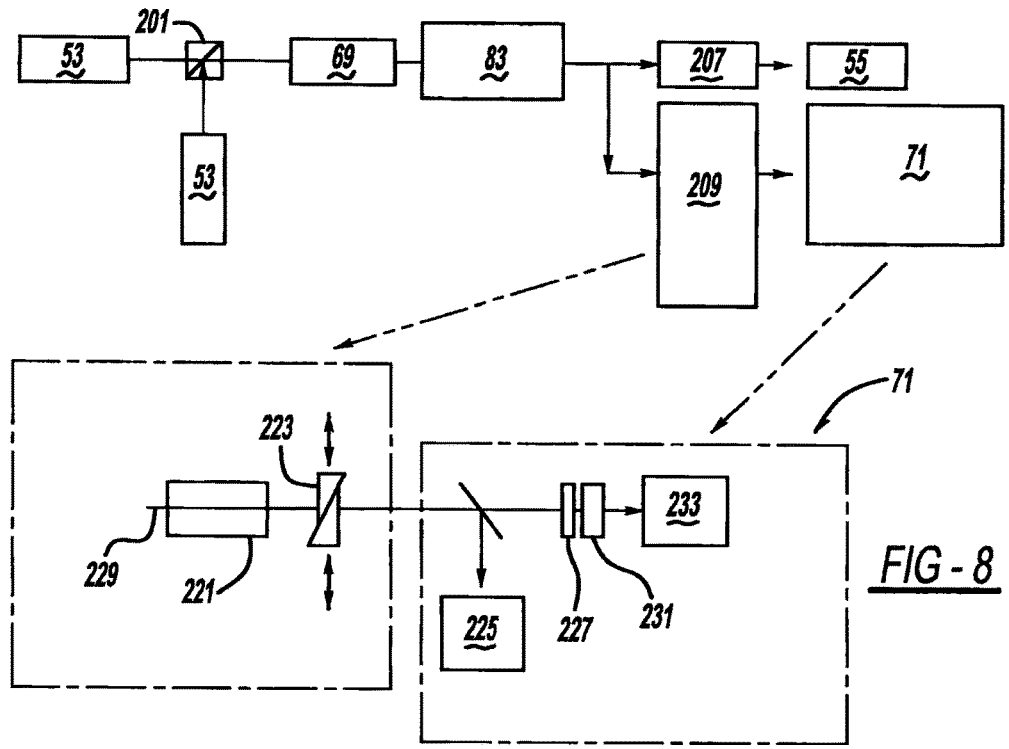
FIG. 8 is a schematic representation showing a real time, chirp correction and pulse characterization unit used with the laser system.

FIG. 8 illustrates the simulation optics module 209 which has components that replicate the dispersion of all optics, and the patient interface, and the specific eye penetration required. The replication optics module 209 includes a large slab of glass 221 with dispersion characteristics similar to that of a microscope objective, used for the surgical procedures. In addition, there is a pair of wedges 223 that are translated by computer control of actuators in order to introduce dispersion expected in the eye tissue 55 for each location. Because the depth of the procedure determines the desired dispersion, the computer controller 63 uses a conversion table previously stored in memory in order to determine and introduce the appropriate amount of dispersion compensation using the pulse shaper 69.

Beam diagnostics module 71 includes a first compact spectrometer 225 that detects a fundamental spectrum of pump laser 53 and confirms a mode locking, central wavelength and bandwidth. A thin SHG crystal optic 227, preferably a 100 micron BBO crystal, is used to generate a second harmonic of the input beam 229. A short pass filter 231 is used to filter out the fundamental light that was not converted into SH and compact spectrometer 233 detects the SHG spectrum.

Slow calibration of the system is required every time a new laser module is turned on (e.g., once a day, once a week, or longer). With the present system, however, this procedure takes less takes between one and five minutes. The system uses the shaper to run MIIPS® and the SHG is detected at the SHG spectrometer. During this procedure the two wedges are translated to their minimum glass position. A compensation mask is then implemented. The main laser beam impinging on the patient interface generates NLO and the shaper runs a chirp scan from −1000 to +1000 $fs^2$ in order to ensure that maximum NLO is obtained at 0 $fs^2$ within an acceptable range of +/−100 $fs^2$. If fine adjustment is required, it is achieved by the controller causing the wedge actuators to move the wedges thereby introducing or removing glass. The typical dispersion of glass is 50 $fs^2$ per mm.

Fast calibration of the system is performed before every procedure (which can be performed in five seconds or less). The objective approaches the patient interface using imaging auto-focus as feedback. Fine adjustment of the procedure is achieved by the controller causing NLO imaging in the form of second harmonic generation or two-photon induced fluorescence of marks in the patient interface. When the surface features are well resolved and maximum contrast is obtained the system is in focus, z=0. The shaper performs a fast chirp scan from −1000 to 10000 $fs^2$ to ensure maximum NLO is obtained at 0 $fs^2$ within an acceptable range of +/−100 $fs^2$. If fine adjustment is required, it is achieved by the controller causing the pulse shaper to introduce a shift in chirp into the pulse shaper main compensation phase. If a major adjustment is needed or if the chirp scan results in a significant nonlinear phase dispersion, then a full MIIPS® scan is required as per the aforementioned slow calibration. The objective is moved to the location of deep marks in the patient interface (e.g., located 1 mm inside the patient interface). The shaper introduces the corresponding dispersion and an NLO image is obtained.

The controller automatically or the doctor manually determines if the focus is sharp enough; if yes, it proceeds, and if not, it fine tunes the z-axis calibration. Furthermore, the controller automatically determines if the NLO intensity is found at the expected dispersion compensation; if yes, it proceeds, and if not, it fine tunes compensation. If it is far off, the controller automatically provides a warning and requires full MIIPS® calibration. This procedure and software provide real-time, feedback closed loop, phase measurement and pulse compression in a portion of the main laser beam.

Figure 9:
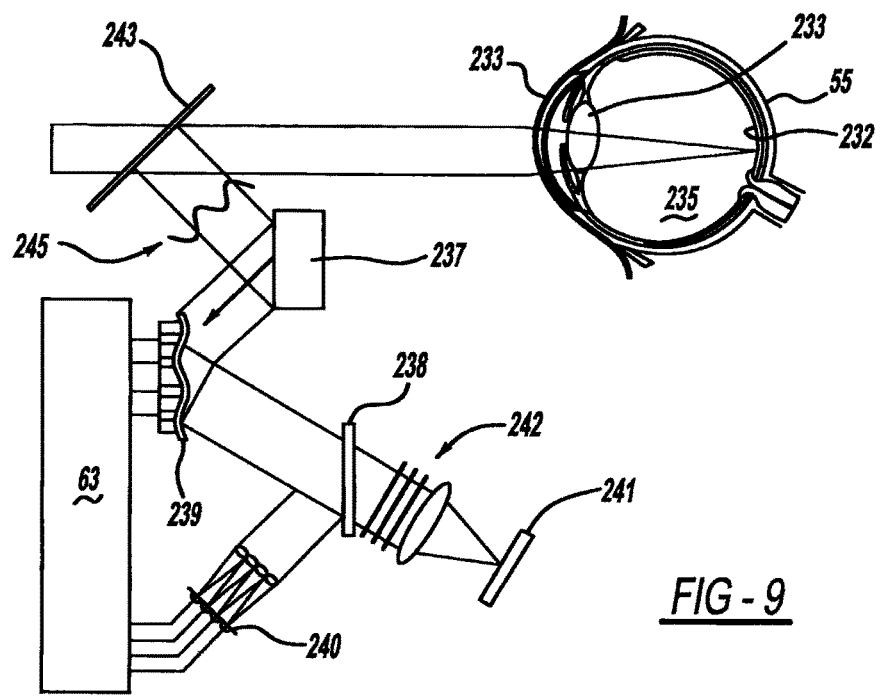
FIG. 9 is a diagrammatic representation showing adaptive optics for wave front dispersion used with the laser system.

Referring to FIG. 9, the acquisition of high resolution images with sub-cellular resolution requires wavefront dispersion correction in the detection module. This assists in imaging retina 232 including the blood vessels, nerves, fibers and adjacent tissues, and uses a femtosecond laser source capable of producing ultrashort pulses in the near infrared. The pulses need to be dispersion compensated because of the dispersion of a cornea 233, lens 234 and vitreous humor 235 of the eye 55. The instrument includes a reflective mirror optic 237, a second beam splitter 238, a deformable mirror 239, a wavefront sensor 240 and controller 63 to correct the sensed phase distortions. A high resolution image capture detector 241 is placed at the location 242 where the wavefront has been corrected. The preferred method for high resolution imaging is a high pixel count CCD, for example a thermo-electrically cooled CCD camera with 20 megapixels. The illumination source for these images is the femtosecond laser that is dispersion compensated. Focusing is selected such that it irradiates a region of desired size and at the desired depth. Two-photon fluorescence and other NLO signals that result from laser excitation is then separated by a dichroic beam splitter 243 and sent to the imaging detector. In this case, the imaging detector has an adaptive optic capable of correcting spatial distortions 245 caused by refractive anomalies in eye 55. Wavefront sensor 240, controlled by controller 63, first measures and then corrects the refractive abnormalities in the eye. Wavefront sensors 240 can be of the form shown with multiple focal arrays, or they can be interferometric. The controller determines the deviations from the plane wave and automatically corrects them through adjustments in adaptive mirror 239. Once the wavefront is corrected, high resolution images of the retina are sensed by the high resolution CCD 241. This approach is being applied for NLO imaging of the retina.

Figure 10:
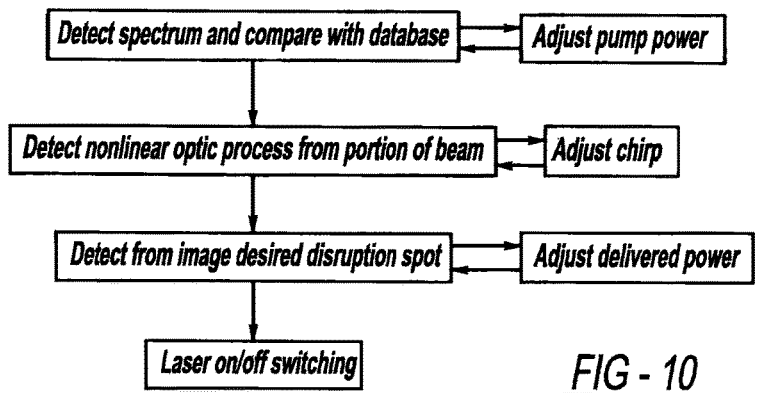
FIG. 10 is a software and method flow chart for maintaining optimal laser performance used with the laser system.

A software program and method used by the controller for maintaining optimal laser performance can be observed in FIG. 10. These steps ensure that the laser is performing exactly within specifications which are desirable for producing consistent results. First, the laser spectrum is monitored by a spectrometer. The intensity and bandwidth of the laser are compared with the spectrum previously stored in the memory database for that laser system. If needed, the pump power of the laser can be increased or decreased in order to match the spectrum. Furthermore, if needed, a small adjustment of the internal half-wavelength plate of the laser can also be adjusted until the output spectrum matches the desired spectrum stored in the computer memory database. The next step is to detect nonlinear optical signals from the laser beam. This involves collecting the second harmonic generation spectrum of the laser obtained when the laser is focused on an SHG crystal. The SHG spectrum provides information about the pulse duration and peak intensity of the beam. The SHG spectrum is compared to one stored in the memory database and if needed, the spectral phase of the pulse is corrected. Finally, the laser is directed at a region of the patient interface where it is tested for ablation. The image of the ablation site is inspected to make sure the laser is cutting as needed. All of these steps can be conducted automatically by the controller interacting with the connected hardware components, with minimal if any user interface, or in a full or partial manually intervening manner by the user.

Laser optimization requires the following sub-assemblies. The pump power to the laser controls the diode pump, which affects the spectrum of the laser output. The chirp adjustment is preferentially achieved by the pulse shaper, but it can also be adjusted by the distance between the gratings or prisms. The laser power delivery for each procedure is modulated by rotation of the half-wavelength plate that is situated in front of the polarizing cube. Finally, the laser on/off switching is achieved by a fast optical shutter. The laser is always operating at optimum pumping power, however, the laser is not always shining on the patient's eye.

Small changes in the pump power are used to adjust the output spectrum. In some cases adjusting the intracavity half-wavelength plate rotation angle may be necessary to improve mode locking. Moreover, the required amount of dispersion compensation can be adjusted by the compensation pulse shaper or by adjusting the distance between the gratings in a pulse compressor. The power delivered to the eye tissue is modulated by rotating the half-wavelength plate that is situated before the polarizer. Again, these can be performed automatically by the controller or with manual user intervention.

Figure 11:
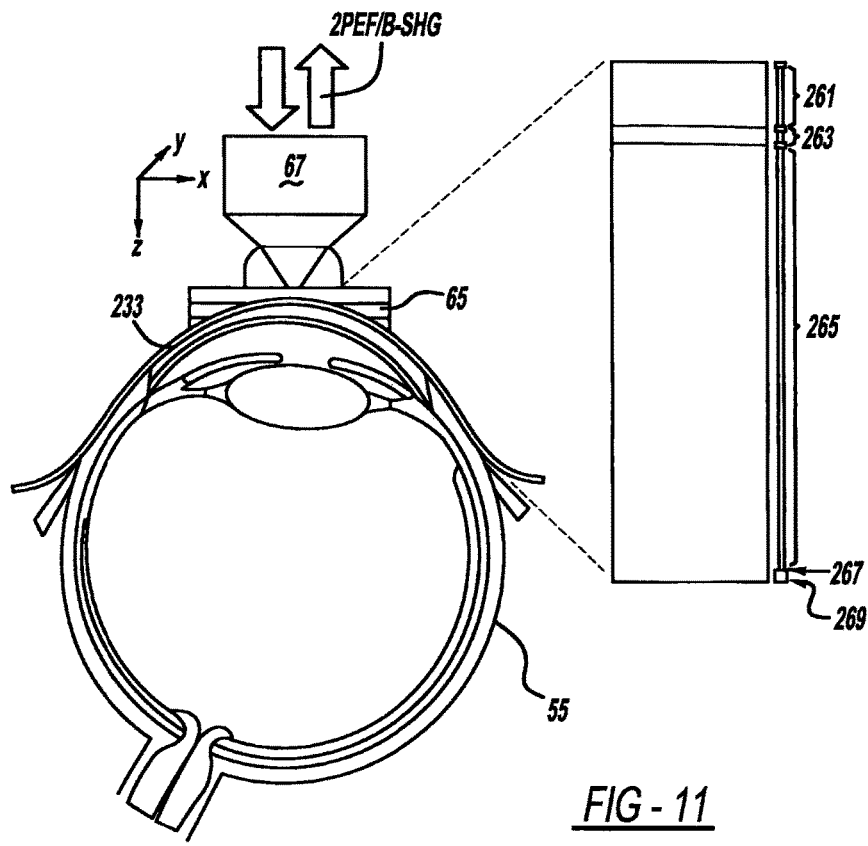
FIG. 11 is a schematic representation showing a multimodal imaging configuration used with the laser system.

FIG. 11 shows how NLO imaging of eye 55 can be used to determine the position of different tissues and structures therein. The laser beam induces the NLO signals such as two-photon excitation fluorescence ("2PEF") and back scattered second harmonic generation ("B-SHG"). The inset on the right shows the cellular morphologies of the different epithelium 261, Bowman 263, stroma 265, Descemet membrane 267 and endothelium 269 layers. These differences and especially the interfaces are easy to detect by NLO imaging. Acquisition is performed parallel to the surface of the cornea 233. Images presented are either the XY acquisitions or the XZ reprojections.

Figure 12A:
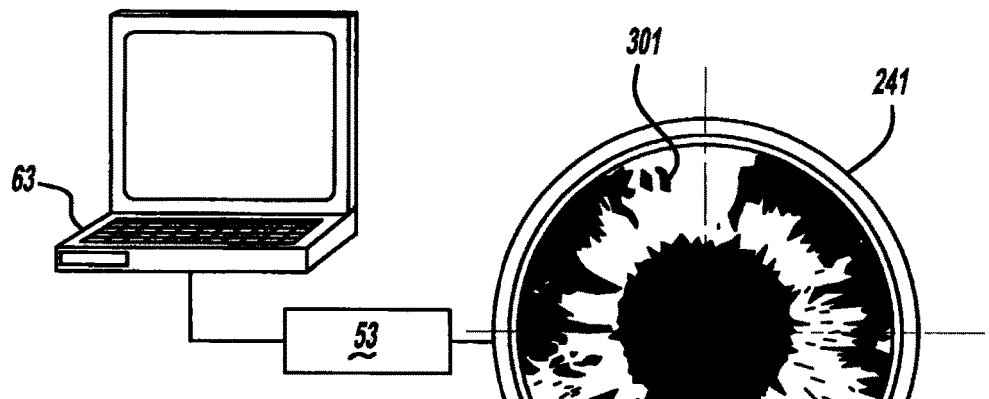
FIGS. 12a-c are diagrammatic representations showing an iris pattern imaging and identification configuration used with the laser system.
Figure 12B:
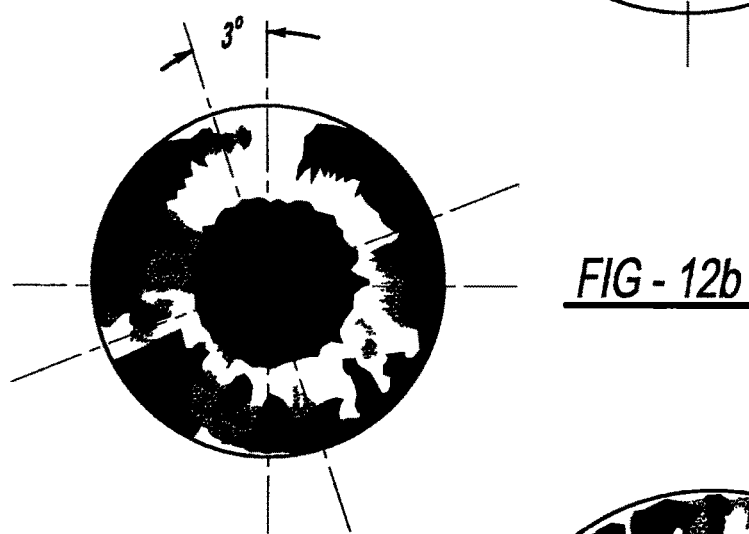
Figure 12C:

FIGS. 12a-c illustrate use of an iris pattern 301 to identify a patient, identify the eye to be treated, refractive parameters and surgical procedure, and/or align the laser system with the eye. It is desirable to make the laser eye procedures less dependent on the skill level of the operators. To address this need, CCD imaging detector 241 senses iris pattern 301 of the patient's eye and the associated controller 63 compares the image signal to an iris pattern previously stored in the computer memory from a prior medical diagnosis session; this automatic comparison allows the computer and/or doctor to confidently identify the patient, the correct eye, and the orientation of the eye to minimize errors of operating on the wrong eye or patient or to correct astigmatism at other than the exact axis. The iris pattern, even when compressed to black and white, can provide sufficient information to determine orientation with respect to the detector to detect better than one degree of rotation resolution. An exemplary method is disclosed in U.S. Pat. No. 7,044,602 entitled "Methods and Systems for Tracking a Torsional Orientation and Position of an Eye" which issued on May 16, 2006, and is incorporated by reference herein.

At the time of the surgical procedure, the previously stored information of the patient is loaded from computer memory and the system obtains a new photographic image of the eye to be treated. The computer performs a correlation analysis between the image stored with the patient file and the image obtained at the time of treatment. If the match is excellent (e.g., >95%) then instrument-to-eye alignment and the surgical procedure proceeds. If the match is equal to or less than 95% then a correlation analysis as a function of rotation is performed by the controller and the degree of change is noted with a warning. The user can then reposition the patient or rotate the axis of the instrument (by software/computer control) in order to make sure that the procedure proceeds as directed by the controller. If rotation cannot improve the match, then the controller determines that this is the wrong eye or the wrong patient record, in which event a warning is given and the system will not proceed unless there is >95% match. FIG. 12a shows a 98% match between stored the iris pattern and currently scanned iris pattern. FIG. 12b shows a 3-degree offset rotation between the stored iris pattern and currently scanned iris pattern, in which event it recommends alignment. And, FIG. 12c shows a 30% match between the stored iris pattern and currently scanned iris pattern wherein the controller provides a warning indicating this may be the wrong eye and requires a user override before proceeding. This iris pattern matching is also well suited to assist in alignment and orientation of the instrument to the eye. Whether it is the iris pattern or three dimensional mapping, the controller uses this scanned eye information to determine and move the rotation, tilt and/or xyz linear positioning of the instrument relative to the eye for surgery.

Figure 13:
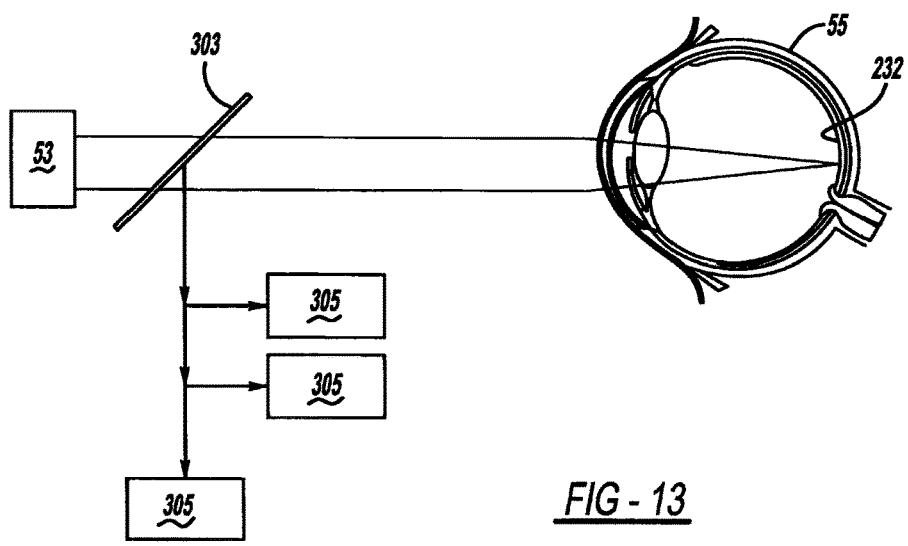
FIG. 13 is a diagrammatic representation showing unstained multimodal retinal imaging used with the laser system.

In the variation shown in FIG. 13, an objective optic is not required for unstained and multimodal retinal imaging and other retinal interventions. Lens 234 of eye 55 will normally focus the laser beam onto retina 232, although an objective with an extra long working distance may be optionally employed for surgery where additional focusing is desired. There is great need for dispersion compensation and for wavefront distortion compensation. A low power ultrashort laser 53, with dispersion compensation, wavefront correction, and temporal focusing capability, emits a set of laser beam pulses, each with a duration less than 150 fs. A mirror 303 directs a portion of the beam to a set of photo-multiplier tube ("PMT") detectors 305 connected to the controller. The use includes diagnostic of macular degeneration (early or for monitoring progress), diagnostic for propensity of a patient to deposit cholesterol and calcium on blood vessels, diagnostic for drugs crossing the blood-brain barrier, diagnostic for glaucoma, pre-surgical diagnostic for retinal deformations, to activate therapeutics at the retina and surrounding tissue and to guide retinal surgery.

The femtosecond laser, centered at 800 nm transmits best through ocular media and is useful in the diagnosis and treatment of retinal disease. High resolution non-linear optical imaging, such as two-photon fluorescence from endogenous compounds such as melanine, xanthynes, FAS, NAD+ and NADH which report on the health of cells and their concentration, has been shown to correlate with cancer. The highest resolution is aided by phase-front correction. While typically a number of different lasers are used for conventional retinal treatment (e.g., Argon, Krypton, Nd:YAG, Er), the femtosecond laser of the present invention can be used to replace all of those lasers. The present laser can be used for imaging with sub-cellular resolution, for inducing photodynamic therapy, for photocoagulation, for cutting tissue, and for ablation. It can be used to open blocked vasculature, and to cause infraction and blockage in leaking arteries. While the fundamental wavelength of the present femtosecond laser is not absorbed by intraretinal blood, xanthophyllis, melanins and other photoreceptor light absorbing molecules, at low intensities two-photon excitation can be used to increase the local temperature and to provide sufficient fluorescence that can be used for imaging and diagnostic purposes. At higher intensities, the present femtosecond laser causes infractions, necrosis and tissue shrinkage. At even higher intensities, the present femtosecond laser is useful for vaporizing tissue and cutting.

Moreover, photothermal effects can be enhanced by the introduction of gold nanoparticles. The surface plasmon resonance of gold nanoparticles is ideal for localizing thermal energy delivered by the laser. Activated surface plasmon resonances have a much larger cross-section than organic molecules and are inherently inert. Furthermore, the nanoparticles are delivered into the eye through injection or conjugated with antibodies that seek cancer cells in the eye, for example.

A major advantage of the present femtosecond laser is the ability to limit the depth at which the therapeutic effects take place and its ability to transmit through the epithelial cells to reach the ganglion cells. The ability to selectively image and treat different layers of the macula lutea makes this laser unique. Alternately, the action of the laser is enhanced by the introduction of dyes that have a strong two-photon excitation cross-section. Furthermore, activation of the dye can induce coagulation of the neovascular complex.

Titanium:Sapphire lasers are well suited for the treatment of macular degeneration and fundus imaging. The ideal laser for these procedures being either the FemtoLaser INTEGRAL element PRO or the Griffin laser from K&M Labs, producing 600 mW of power centered at 800 nm with a bandwidth exceeding 100 nm, compressible to sub-10 fs pulses. It is envisioned that future Er fiber lasers when frequency doubled will be able to produce 10 fs pulses at 780 nm. For most procedures, the laser is attenuated to less than 10 mW.

Figure 14B:
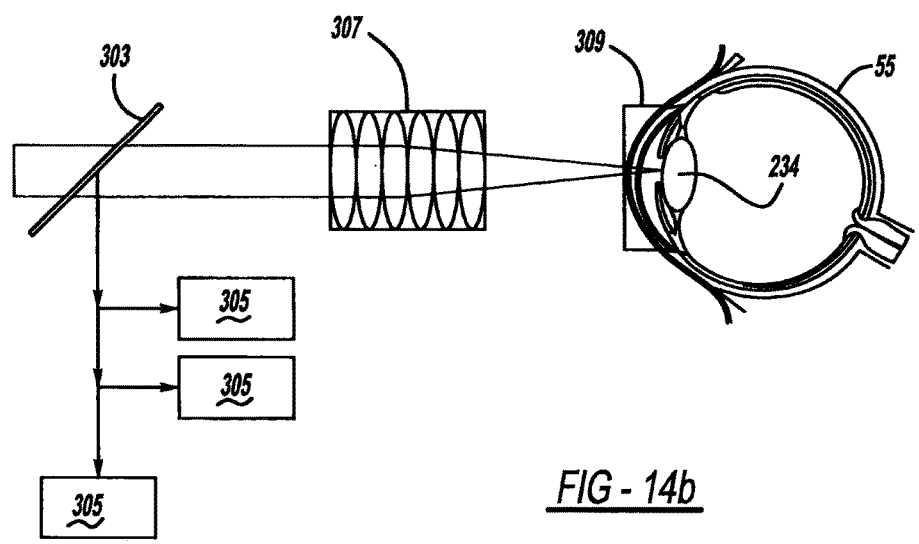
FIGS. 14a and b are diagrammatic representations showing unstained and nonlinear optical imaging for dimensional mapping and distance calibration used with the laser system.
Figure 14A:
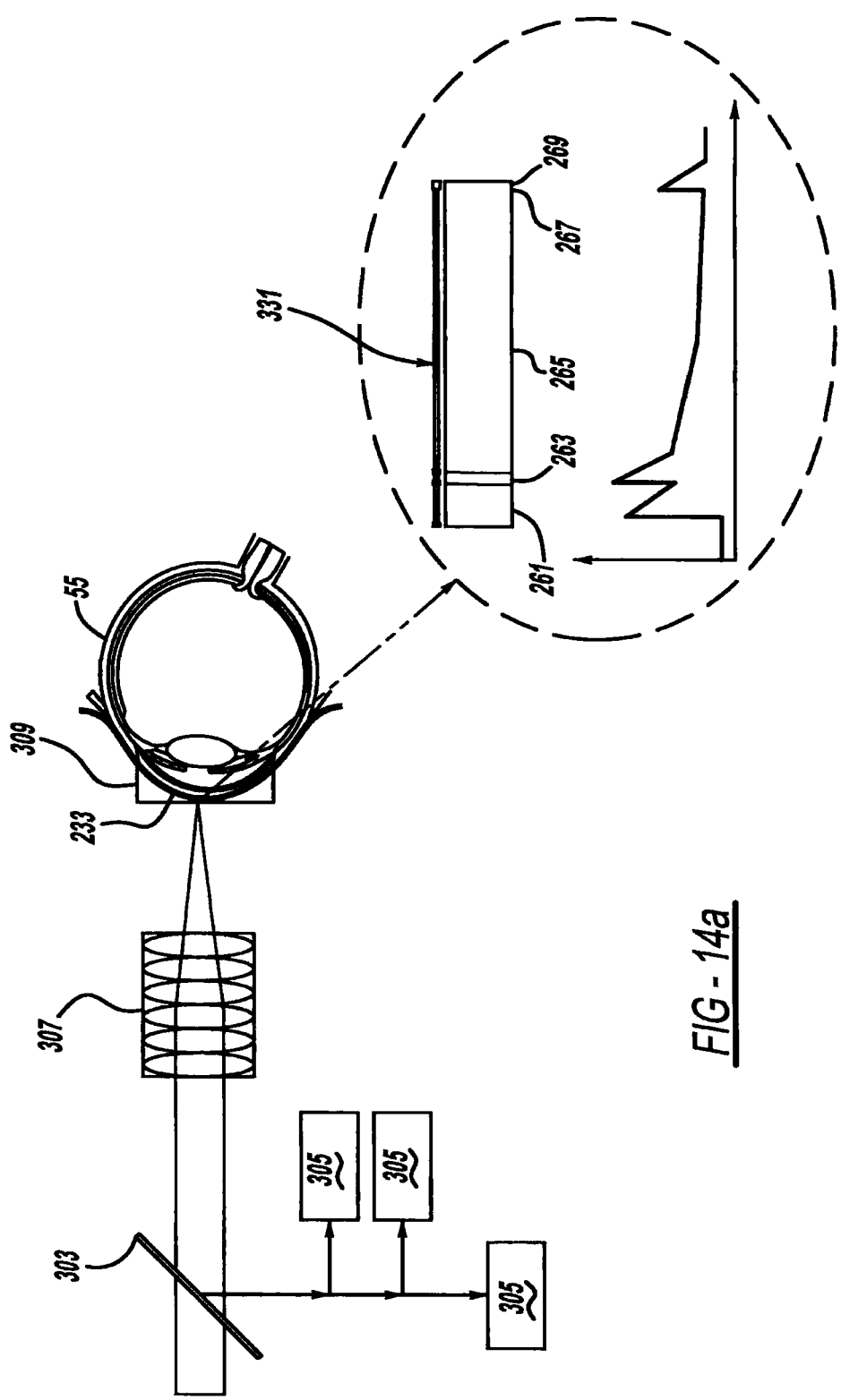
Figure 15:
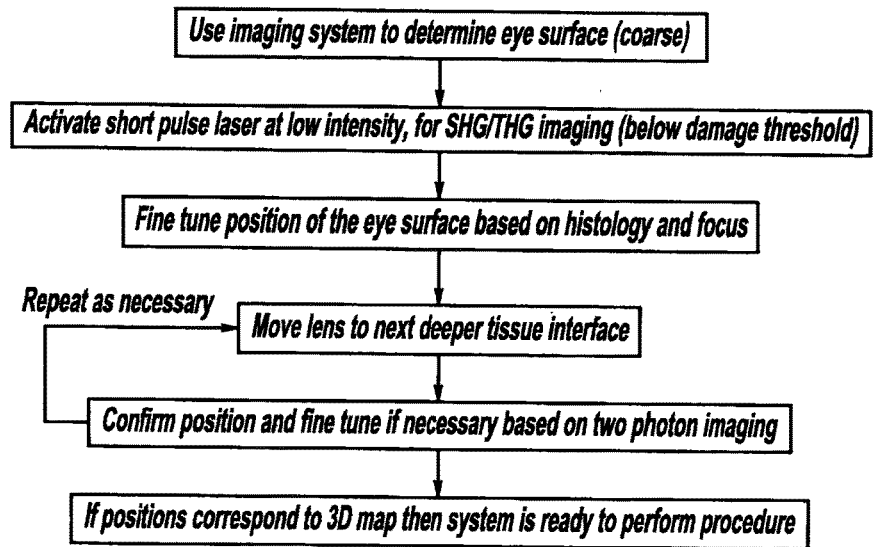
FIG. 15 is a software and method flow chart for distance calibration used with the laser system.

FIGS. 14a-14b and 15 illustrate using unstained NLO imaging for 3D mapping, distance, calibration and feedback. Thus, NLO imaging is used instead of OCT. An objective lens 307 is in the laser beam pulse path between mirror 303 and interface 309. A set of computer controlled galvonometers 400 (see FIG. 30) changes the xy position by changing the angle of the mirrors mounted thereto, and the z position is charged by the controller causing linear translation of the microscope objective toward and away from the eye. NLO imaging does not require interference between forward and backward laser light. One photo-multiplier tube ("PMT") 305 is for fluorescence detection, a second PMT is for SHG detection and the third PMT is for third harmonic generation detection. PMTs, or alternately avalanche photodiodes, detect total intensity. Thus, intensity is collected for each xy position to create an image by the controller.

Figure 16:
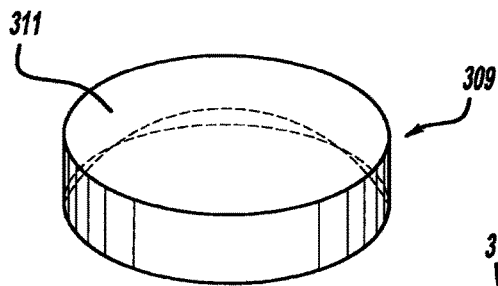
FIG. 16 is a perspective view showing an NLO compatible patient interface.
Figure 17:
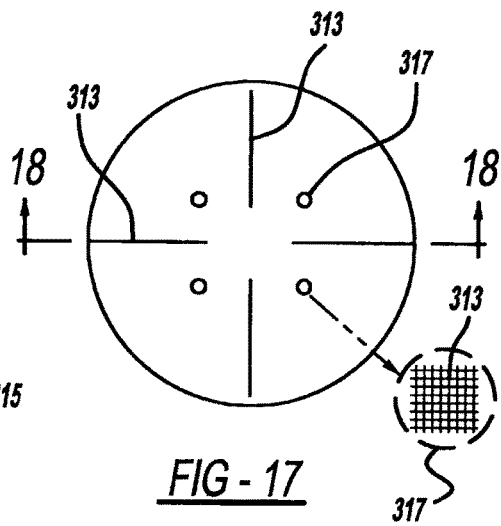
FIG. 17 is a true elevational view showing the NLO compatible patient interface used with the laser system.
Figure 18:
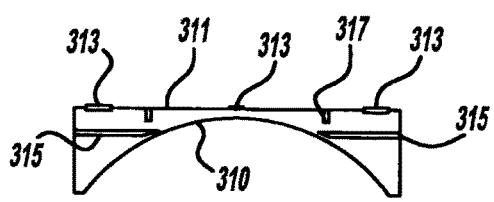
FIG. 18 is a cross-sectional view, taken along line 18-18 of FIG. 17, showing the NLO patient interface used with the laser system used with the laser system.

In FIGS. 16-18, a concave surface 310 of interface 309 fits onto the cornea of eye 55. An outer surface 311 of patient interface 309 has short linear markings 313 that allow accurate z determination by the controller based on sensed signals from the detector(s). Patient interface 309 also has embedded longer linear markings 315 for depth calibration; for example, these markings 315 are 1 mm below surface 311. Alternately, or in addition, circular markings 317 project approximately 3 mm or less from surface 311. Crossed and various other markings can alternately be used. The patient interface can be thought of as a contact lens that has on it surface markings that are very bright when imaged by an NLO microscope. Surface 311 may be substantially flat or have the same curvature as surface 310 and has an anti-reflective coating for the wavelength of the laser. The marks at the top and at different depths allow the system to calibrate an xyz axis of motion. Marks 313 are made of a compound with a high NLO cross-section. Exemplary compounds include a dye like fluorescein or rhodamine, or zinc oxide, and could include microscopic laser ablation marks without the use of a special compound. Embedded marks 315 are made with a similar laser 53 at the factory and are simply ablated portions, the interface of which will emit a strong SHG signal. Concave inner surface 310 fits the patient's eye size.

Patient interface 309 further permits testing of the laser ablation mode without injury to the eye. Each tissue has a different NLO structure and signal and, each tissue interface has a strong SHG. NLO imaging is used to create a new 3D map for surgery and the NLO imaging is used to also confirm the 3D map and coordinates for surgery.

At a specific depth, the fs-laser is scanned by a pair of mirrors on galvanometers, in the xy plane and for each xy location, a nonlinear optical signal is collected by the PMTs. The NLO signal, is, for example but not limited to, two-photon induced fluorescence, second harmonic generation or third harmonic generation. The multiphotonic NLO signal is generated only where the threshold peak intensity is achieved, and this is only at the location of the focal spot. This ability is employed for calibrating the z (depth) axis which corresponds to the distance between the objective and the eye of the patient. For most surgical procedures in the external part of the eye, especially those involving the cornea and lens 233 (see FIG. 14b), patient interface 309 helps to center eye 55, and provides a shield for the laser optics.

Upon first approach, the system uses regular photographic imaging to search for the distance of optimal focus on the surface features of patient interface 309. The system then scans the laser in a raster scan pattern with an intensity that is lower than the threshold for material modification or ablation. As the laser is scanned, the NLO signal is collected by PMT detectors 303 and an image is created by the associated controller. The rate of image collection varies from 1-30 images per second. The system locates one of the surface features or markings 313 on patient interface 309 and scans a smaller region, thereby speeding up the process of finding the location of surface 311. The goal is to find when the surface features or markings come into focus and to register that z-axis location. A full image is then obtained to make sure that surface 311 is horizontal (or normal to the laser assembly), and the center of the eye is located. The second step is to find features or markings 315 that are embedded in the patient interface. Finding these requires the translation of objective 307 towards patient eye 55 by the marking depth and then to do a fine approach while tracking the focus when the features become sharp. This can be done automatically by the controller or with manual intervention. At that point, the system calibration is set. Because the patient interface dimensions are well known and it is in physical contact with the eye of the patient, the controller now can automatically calculate and create a three dimensional model of the eye based on the size, curvature and any other characteristics of the eye of the patient and a model with typical parameters for human eyes.

For certain surgeries it is desirable to have a three dimensional map with accuracy better than 10 microns. In this case, it will be important to ascertain the depth of the different tissue interfaces. This step takes into account the fact that NLO signal, and in particular SHG and THG, is strongest from interfaces. At certain locations, objective 307 is scanned in the z direction towards the eye while the NLO signal is detected by at least one of the three different detectors 305. Changes in the amount of signal near the expected changes, as the focal plane traverses the epithelium, stroma, endothelium, lens capsule and lens layers 331. The controller correlates this data with a model of the eye, and this serves to calibrate the three dimensional model of the patient eye. Similar depth scans can be carried out at different x-y points approximately 1 mm apart.

Distance calibration (for on board OCT or NLO imaging) can be observed in the software and method steps of FIG. 15. Depth determination is necessary for most laser eye procedures. For example, for cutting a flap in the stroma, it is preferred to have depth resolution better than 10 micrometers. In some cases, when the cornea has been damaged by accident or because of a disease, it is necessary to use internal structures as a reference because the surface of the eye is not smooth. This procedure details the initial approach of the system and the three axis calibration. The first step is carried out using photographic imaging as it evaluates the sharpness of features in outer surface 311 of patient interface 309. Once the coarse approach has been completed, the system then activates the short laser pulses at low intensity and obtains a series of nonlinear optical images at a range of heights. The images are evaluated by the software and the xyz axes are calibrated. At this point a higher resolution NLO image of the epithelium of the eye is performed and confirmed based on histology and sharpness of focus. Subsequently, the system performs a series of z scans in order to map deeper tissues that will be involved in the surgical procedure. These scans serve to confirm and update the three dimensional map for the eye that will be used to perform the desired surgical procedure. This method will allow the design of custom corrections for eyes that have been damaged.

Figure 25:
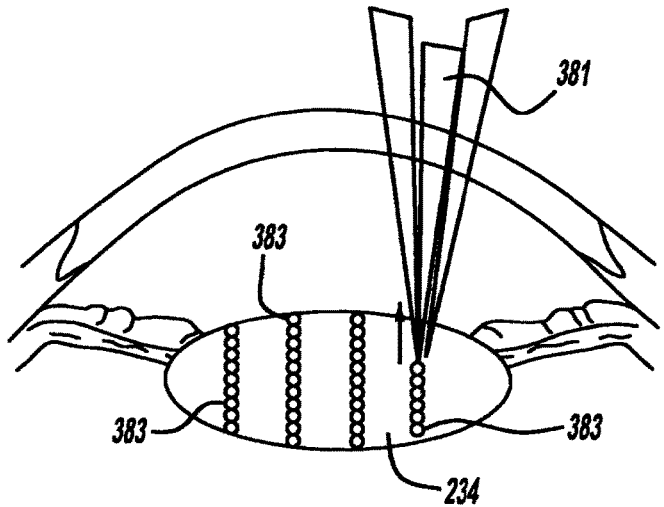
FIG. 25 is a diagrammatic representation showing one-piece lens removal used with the laser system.
Figure 26:
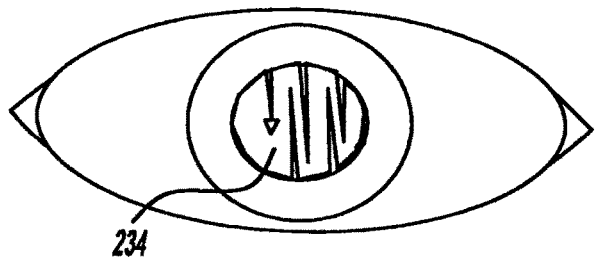
FIG. 26 is a diagrammatic representation showing one-piece lens removal used with the laser system.

FIGS. 19-22 show a variation of an NLO compatible patient interface 351 which includes transversely elongated access ports for surgical intervention. Each access port 353 is defined at an outer end by a hole in a peripheral side wall 355 of interface 351, and at an inner end by a hole where the port intersects a concave inner surface 357 that fits against cornea 233 of eye 55. Access ports 353 make it easy to introduce surgical instruments 359 (see FIG. 27) to pull out tissue, such as a damaged or opaque lens or lens nucleus 234, and to insert grafts or an intraocular lens. The access ports can also be optimized for all laser refractive correction surgery facilitating the removal of tissue such as a lenticule or the lens once it has been cut as shown in FIG. 25. Interface 351 also has markings 361 on an outer surface 363 and embedded markings 365 and/or bore markings 367.

Figure 23A:
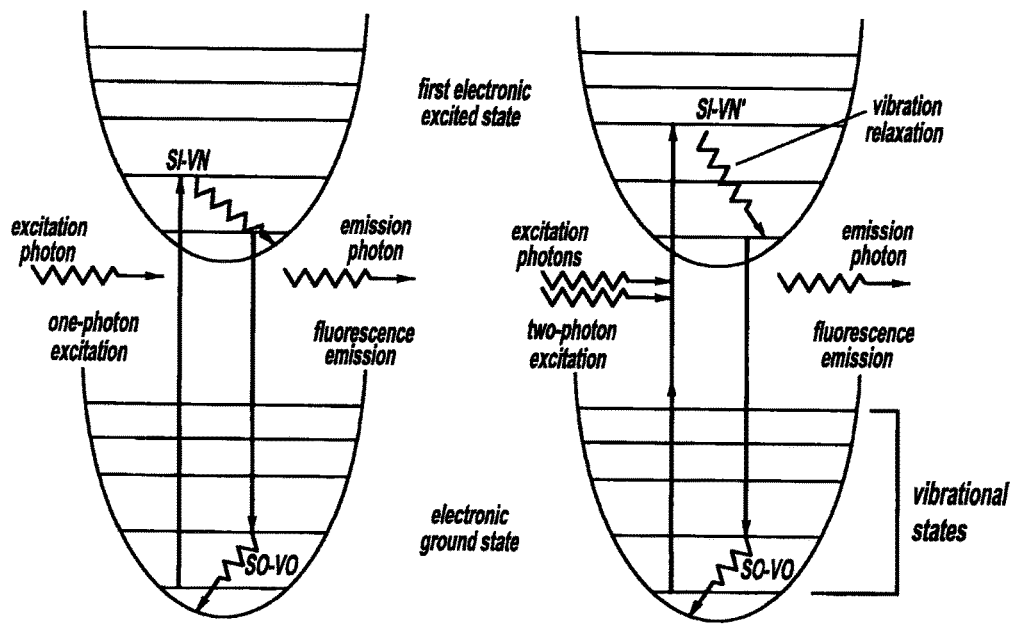
FIG. 23a is a diagrammatic representation showing two-photon fluorescence used with the laser system.
Figure 23B:
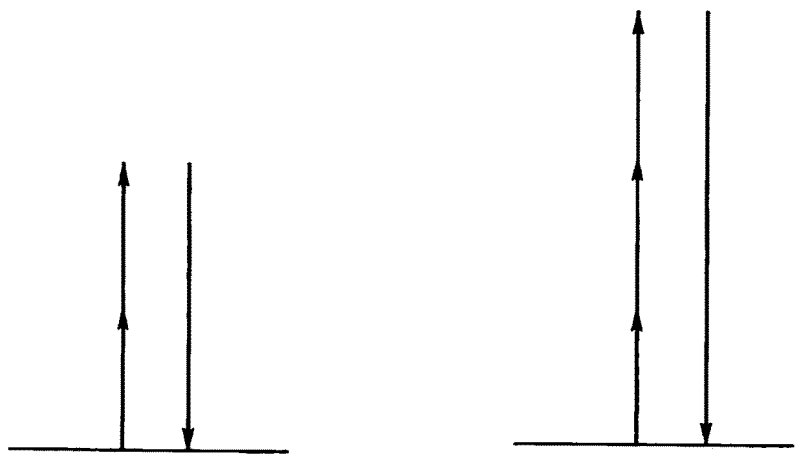
FIG. 23b is a diagrammatic representation showing second and third harmonic generation energy levels used with another variation of the laser system.

FIG. 23a shows Jablonski diagrams for one-photon (left) and two-photon (right) fluorescence. NLO, including multiphoton or multimodal imaging, includes two-photon fluorescence emission imaging; two-photon and three photon imaging is possible because there are naturally occurring compounds in the eye that fluoresce in visible light when excited by the present ultrashort and near-infrared pulses. Second harmonic generation ("SHG") imaging (shown at the left of FIG. 23b) involves the creation of a frequency that is twice the incoming frequency. This process occurs primarily from media that lacks a center of inversion. There are proteins such as collagen that generate significant second harmonic light to permit imaging with the present system. Third harmonic generation ("THG") imaging (see the right side of FIG. 23b) involves the sum of three frequencies within the bandwidth of the pulse to create a frequency corresponding to the sum. THG is primarily generated when the focal plane crosses an interface. Therefore, THG in the present laser system is as accurate or better than optical coherence tomography to determine the depth, location, measurement, or characteristic of different portions or features of the eye.

Reference should now be made to FIGS. 25-28, 30 and 40. An accordion, spiral or other contiguous cutting of lens 234 or the nucleus of the lens is done by the laser beam pulses 381 so that it can be collapsed and removed in one piece. This removes the need for rinsing and tediously chasing every small bit as is typical for conventional phaco chopping and/or ultrasound procedures that break the lens into many fragments. The present approach is to cut the lens into one continuous segment so that it can then be easily and quickly pulled out, leaving no residue. When using temporal focusing, the depth of the cut is limited which provides greater z control. As shown in FIG. 25, it is preferred that the laser beam cuts 383 are made from the bottom up in order to avoid any refractive or scattering distortion that could be caused by regions where the laser has already acted and ablated the tissue. The use of ultrashort pulses prevents the excessive formation of bubbles that disrupt the cutting process.

FIG. 29 depicts the use of temporal (spectral) focusing for achieving high depth resolution during retinal laser treatments. Different frequencies or colors of the temporally chirped, ultrashort pulse are reflected by a mirror 391, diffracted by a grating 393, collimated by another grating 394, separated at a first scanning mirror 397 and reflected by a second scanning mirror 399. The beam is thereafter focused by a thin lens 401 to fine tune the depth of the actual focal plane or target point. A CCD imaging detector 241 is also employed. Only at the focus, do all the frequency components of the laser overlap. Therefore, the pulse behaves as a long pulse everywhere except at retina 232 where it becomes an ultrashort pulse and it is capable of inducing nonlinear optical signals or to be used as a surgical instrument for cutting. The spectral focusing prevents the pulses from harming the adjacent tissue that receives the unfocused pulse energy.

Figure 30:
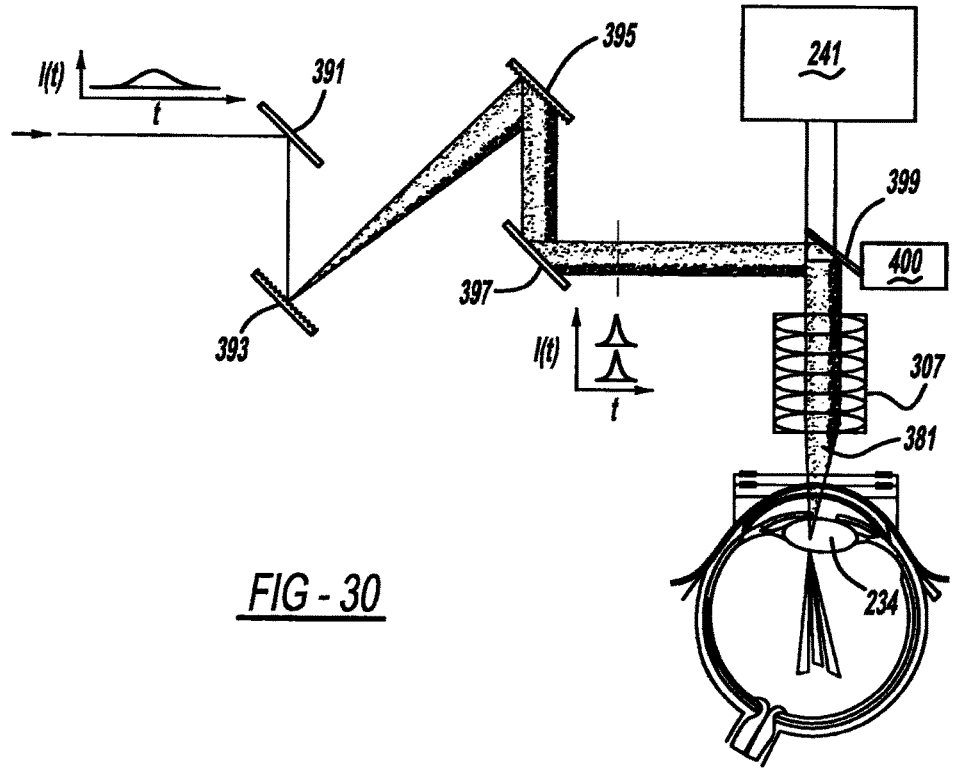
FIG. 30 is a diagrammatic representation showing temporal focusing for cataracts and refractive correction used with the laser system.
Figure 31:
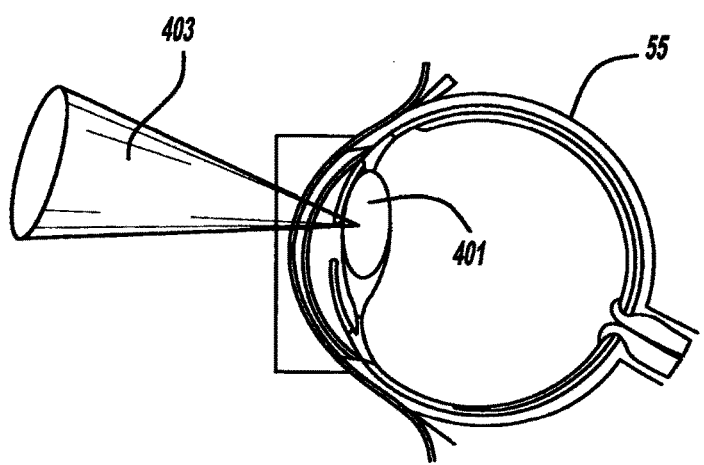
FIG. 31 is a sectional view showing cataract surgery used with the laser system.

As can be observed in FIG. 30, the concept behind spectral focusing is to spread the frequencies of the pulse in such a way that they only overlap at the focal plane. For this method to work it is desirable to control the initial chirp of the pulses because the pair of gratings 393 and 395 used to disperse the pulse introduce negative chirp. A laser pulse with positive chirp is directed to first grating 393 where the frequencies disperse and then second grating 395 oriented so that the dispersion is stopped and the beam is collimated. Mirrors 399 direct the beam towards focusing objective optic 307. Mirrors 399 and objective 307 are moveable and their position is controlled by the computer. All the frequencies of the pulse overlap in space and time at the focal spot coinciding with lens 234 of the eye where the maximum peak intensity is achieved. This method is compatible with all nonlinear multiphotonic optical methods such as SHG and THG imaging as well as ablation and other material modifications. Temporal focusing does not work with long duration pulses. Thus, it is preferred that the pulse durations be less than 100 fs, and even 10 fs, so that there is sufficient bandwidth to spread out. It is noteworthy that temporal focusing has additional benefits since the laser causes no damage outside of the focal volume and it enhances the depth (z axis) resolution. Furthermore, temporal focusing avoids self-focusing, self-phase modulation and other optical distortions that are common to intense pulses traveling in condensed media which is particularly desirable for retinal surgery.

The localization of a replacement intraocular lens 401 ("IOL") is highly desirable. This is traditionally manipulated by hand with surgical instruments. The present laser system, however, is able to finely adjust lens 401 noninvasively using a laser beam pulse 403, as shown in FIGS. 31-35. The laser can "stiffen" or "loosen" the arms of the IOL to achieve fine positioning. The fine tuning procedures can occur during the surgical procedure, such as modifying or moving a radially extending attachment arm 405 of IOL 401, as shown in FIG. 32. The laser can be used for two-photon curing or polymerization of a viscoelastic polymer 407 in IOL 401 to modify the local index and tensile modulus, as shown in the FIGS. 31, 33 and 34. When needed, these procedures can also be performed a few days post-surgery once eye 55 has healed. With the aide of the present retinal imaging and laser adjustment of position and refractive power, the patient can achieve excellent vision, better than 20/20.

With these IOL modification procedures, the refractive laser power should be adjusted by two-photon excitation in order to protect from UV light such as would come from sunlight. IOL 401 is provided with a UV blocking filter 411 (see FIG. 35). This filter permits only two-photon processing to be used for adjusting the refractive power of the lens. The photo-refractive region is limited to a certain thickness and region in the IOL. Accordingly, the major correction is achieved by choosing the appropriate power and fine adjustment is achieved by the laser procedure. Once the IOL is inserted, the patient interface is removed and the patient and the imaging capabilities of the eye are evaluated by image formation on the retina. The refractive correction required for perfect vision is measured and the required fine tuning is determined. If significant changes are needed then the less than 100 fs laser pulses are used at an intensity that is well below the threshold for ablation but sufficient to induce two-photon excitation. Multiphoton (e.g., two-photon) induced refractive index change through polymerization or chemical cross linking modification is performed in the necessary regions in order to obtain the desired refractive change. Thereafter, the imaging capabilities of the eye are evaluated. If it is still not acceptable, a new refractive correction procedure is performed and evaluated. This fine tuning procedure can be repeated days and weeks after the initial surgery to make sure that the patient achieves the highest degree of vision possible. Alternately, a laser emitting pulses each having a duration of less than 1 ps can be used although all of the advantages may not be realized.

Figure 24:
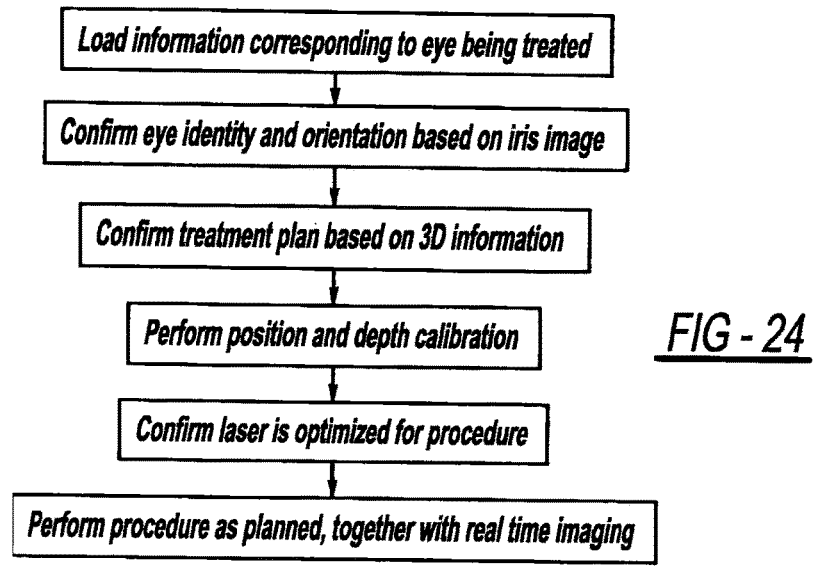
FIG. 24 is a flow chart showing a surgical method used with the laser system.

Typical surgical and software steps are shown in FIG. 24. The procedure may involve the cutting or bleaching of tissue in the stroma or the lens of the eye. The initial step is to enter the information of the patient and to display the information on the computer screen about the eye to be treated. As previously discussed, the system then takes a photographic image of the eye under the laser system and a confirmation routine is used to match the iris pattern on file with the eye presented by the patient. If the match is good, then the treatment can proceed. If the match is not sufficiently high, then a warning is given to the doctor. The next step in the procedure is to confirm a treatment procedure based on a three dimensional map of the eye. The instrument needs to know the absolute position of the tissues to be treated. This three dimensional treatment map can be formulated based on optical coherence tomography or more preferably, nonlinear optical imaging information. The doctor can review the procedure at this point. Once the treatment is accepted, the instrument performs an in-situ calibration to make sure that it is able to locate the different tissues in the eye with a resolution that is on the order of 10 micrometers. Once the coordinates are calibrated and the laser performance is confirmed, the procedure takes place as planned. The procedure can proceed entirely automatically or it can be supervised and even directed by the surgeon. At all times, real time imaging is provided in the screen for the doctor to monitor the progress.

Figure 36:
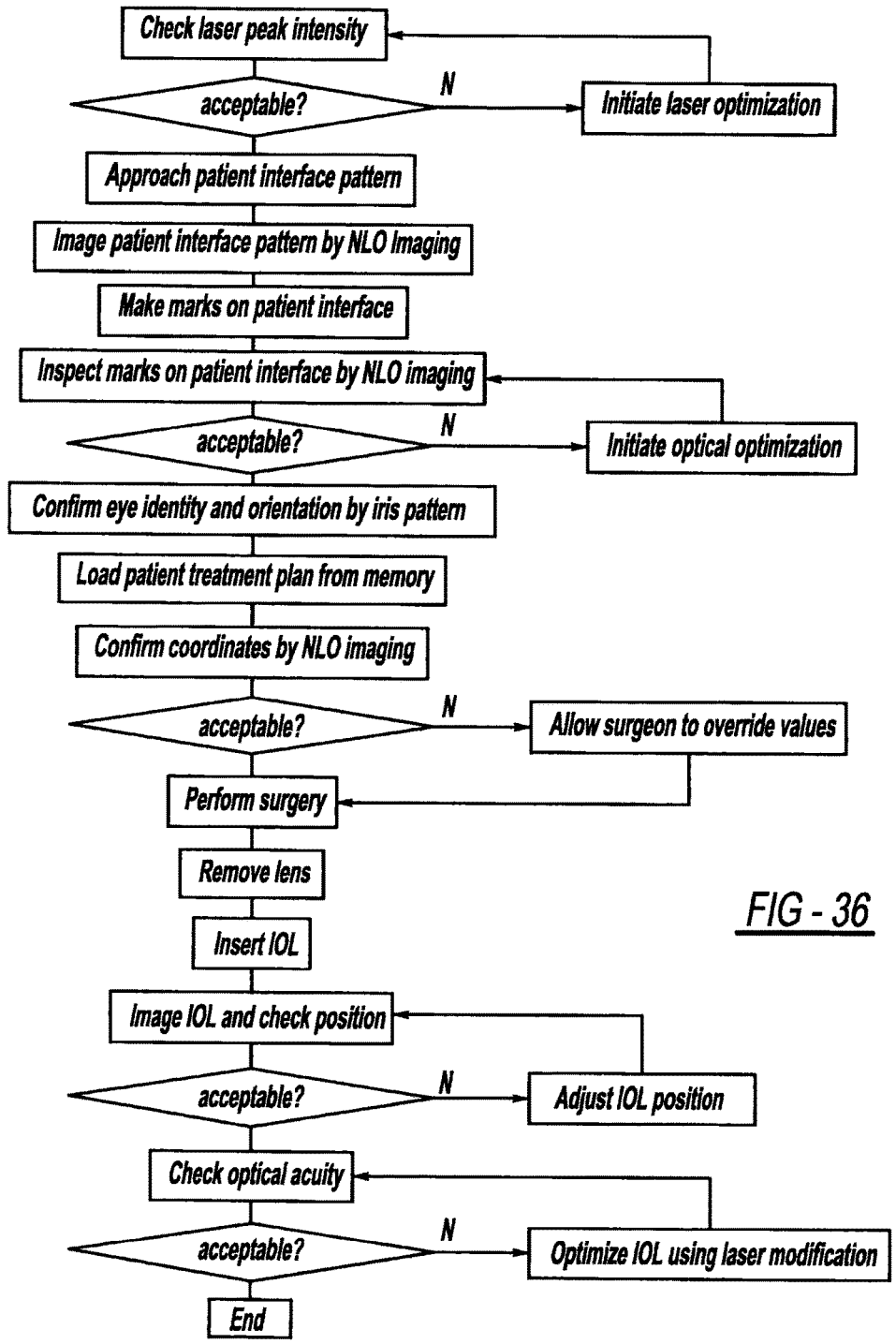
FIG. 36 is a software and method flow chart for automated cataract surgery used with the laser system.

Surgical and software steps for automated cataract surgery are shown in FIG. 36. The first step is to check the performance of the laser, in particular its peak intensity. If it is acceptable then the instrument approaches the eye and the patient interface top surface patterns come into focus. The laser is then used at low intensity in order to image the surface features using the NLO signals. This allows the system to calibrate the height and position of the patient with very high (better than 100 micro meter) resolution. The laser then makes marks on the patient interface by using a pulse intensity above the threshold for ablation. The imaging system inspects the marks made on the patient interface using NLO imaging. If the marks are of poor quality then optical calibration needs to be refined. The next step is to confirm the eye identity and orientation by checking with the iris pattern of the patient stored on the computer file. Once confirmed, the previously input and stored patient treatment information is loaded from the memory and displayed. The system, using low laser intensity, performs a series of z-scans in order to confirm the depth and position of the different tissue interfaces. Once confirmed, the doctor reviews the treatment plan and manually confirms it or enters modifications into the keyboard of controller. The system then performs the desired surgery. Once the lens has been cut, the surgeon inserts a tool through the access port of the patient interface to grab the lens and pull it through the port as essentially one piece. Once the lens is removed, an intraocular lens is thereafter inserted. Subsequently, the system images the eye to confirm the position of the IOL. If needed, the position of the IOL can be adjusted manually using a mechanical tool or it can be adjusted using the laser by softening or stiffening the positioning arms of the IOL. The system then checks the actual optical acuity of the patient. If needed, the optical acuity can be optimized by using the laser to change the refractive properties of the replaced lens. This fine tuning can be used to make sure the patient achieves 20/20 vision. These steps can be performed automatically by the controller interfacing with the hardware components (or their actuators), or fully or partially through manual intervention of the user.

Figure 37:
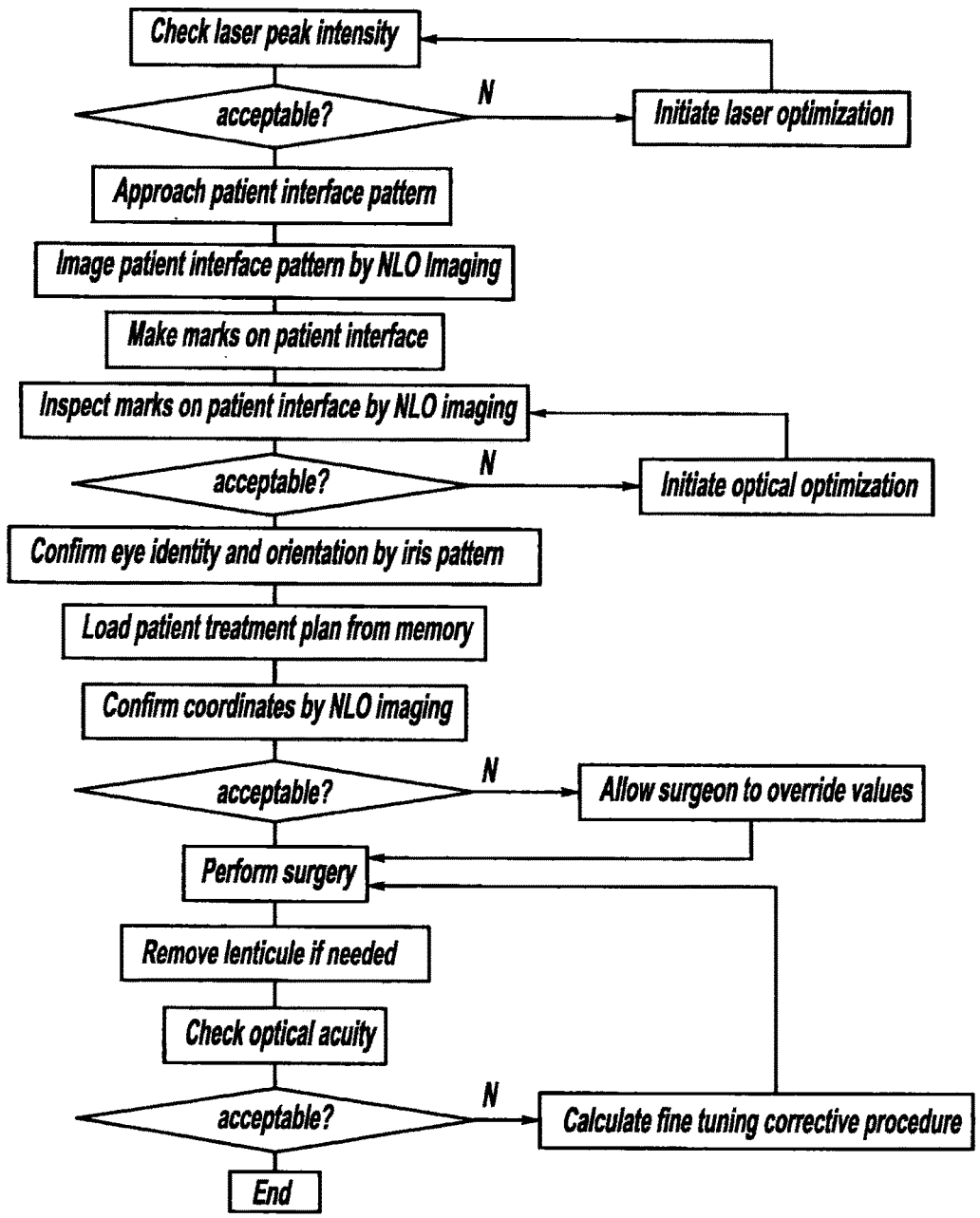
FIG. 37 is a software and method flow chart for automated femtosecond refractive correction used with the laser system.
Figure 38:
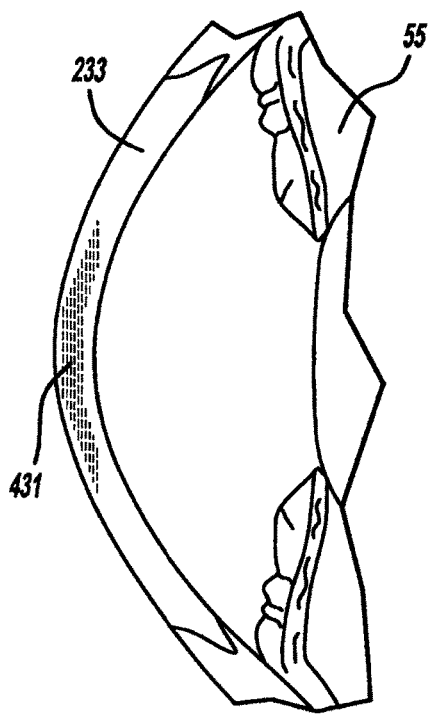
FIG. 38 is a diagrammatic sectional view showing intrasomal refractive modification used with the laser system.

FIG. 37 shows surgical and software logic steps for Automated femtosecond-laser refractive correction. Reference should also be made to FIG. 38. In some cases non-invasive intrasomal modification is possible and then there is no lenticule that needs to be removed. The laser is able to cause sufficient refractive change in the cornea and there is no need to remove a lenticule. The application of riboflavin is known to cross link the collagent when activated with UV light. In this case, the ultrashort pulse laser activates the riboflavin or other similar compound by two-photon excitation in order to make the refractive changes to the cornea permanent. Traditionally, when a lenticule needed to be removed, this required two incisions, one for the tweezers to be introduced and one on the opposite end of the eye to permit fluid motion and prevent a vacuum that would not allow the lenticule to be removed. The present method for refractive correction uses only the on-board femtosecond-laser to achieve the refractive correction. The doctor positions the patient and fits the patient with the appropriate patient interface. The laser peak intensity is checked to make sure it meets the specifications and if not, the laser is re-optimized. Once the laser is performing as required, the system approaches the patient interface while using the photographic imaging. Once the patterns on the surface of the patient interface are in focus, the system switches to high resolution calibration mode. At this point NLO imaging is used to image the patterns of the surface of the patient interface. Then the laser is increased in power and marks are made on the sides of the patient interface; those marks are inspected. If they are within the range of acceptable performance then the system is ready. If not, the laser optical system is recalibrated and new marks are made and evaluated. Once the laser is ready, the patient and eye identity are confirmed by the iris pattern. The patient file is loaded into memory and the system performs a series of images as a function of depth in order to confirm the location of the different eye structures. At this point the system displays the prescribed treatment and asks the doctor to approve the treatment or to override some of the values. Once confirmed the surgery is performed automatically wherein a series of laser ablations for intrasomal modification are made at area 431 of cornea 233. At the end of the intrasomal ablation, if a lenticule has been cut and needs to be removed the system performs cuts at opposite sides of cornea 233 to allow lenticule extraction using a mechanical tool that can be inserted at the access port of the patient interface. At the end of the procedure the optical acuity is checked by the same unit projecting a pattern into the retina. If the acuity is acceptable the treatment is completed, or if needed, additional treatment of the stroma can be performed until best vision is obtained. This approach should allow refractive corrections of one half or less than one half of a diopter. These steps can be performed automatically by the controller interfacing with the hardware components (or their actuators), or fully or partially through manual intervention of the user.

Figure 44:
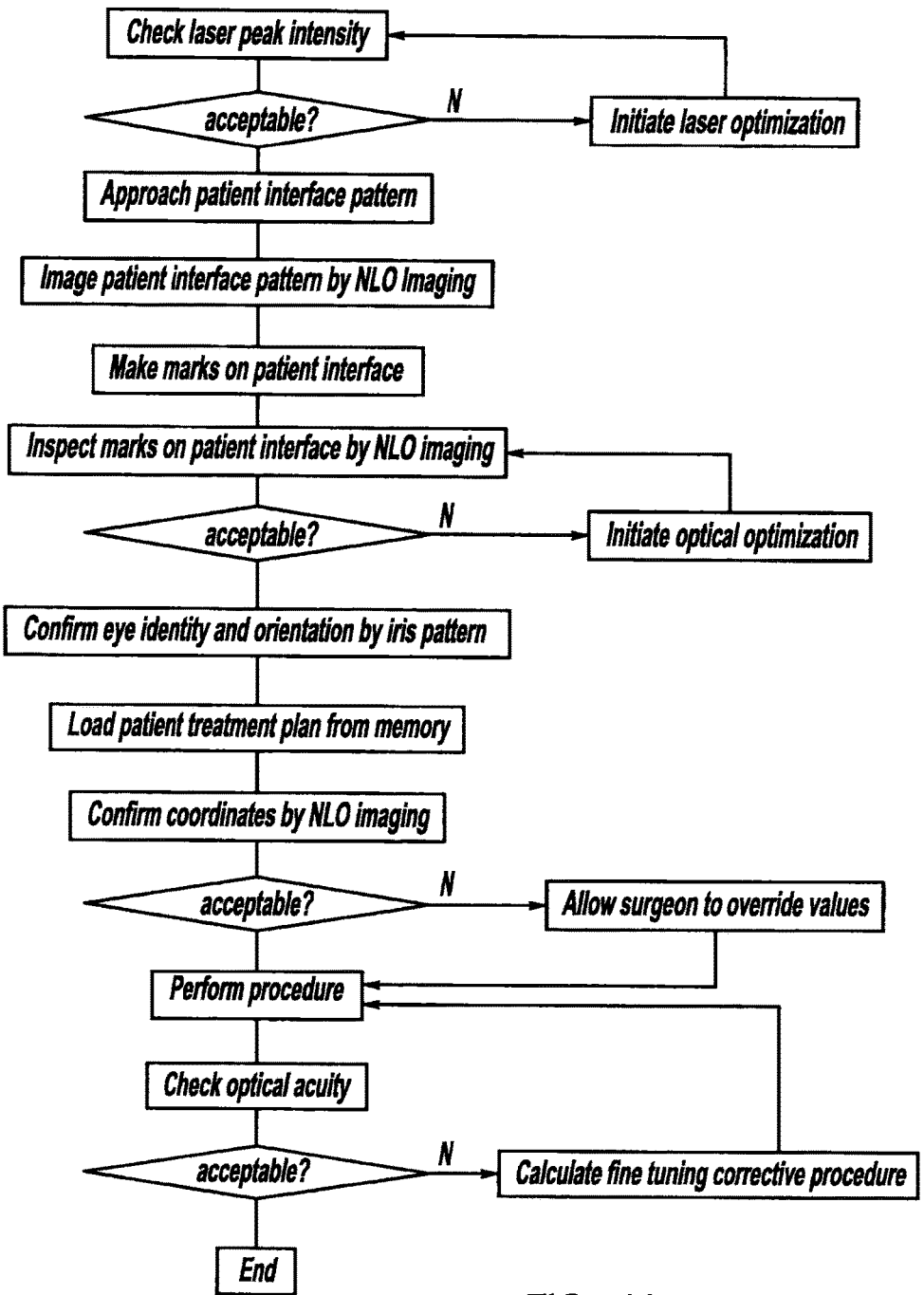
FIG. 44 is a software and method flow chart for non-invasive modification of a lens for presbyopia or correction of cataracts using the laser system.
Figure 45:
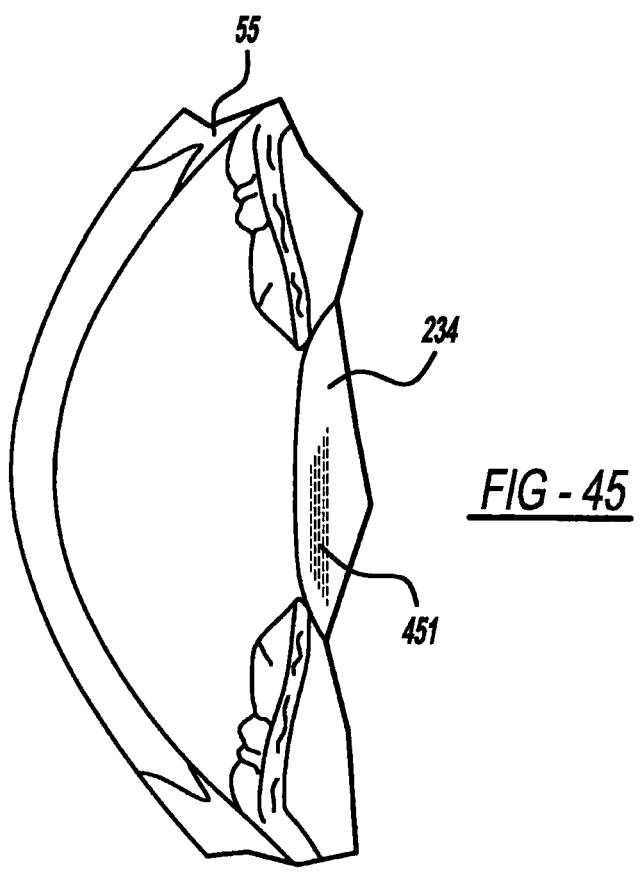
FIG. 45 is a sectional view showing non-invasive refractive lens modification using the laser system.

The non-invasive modification of lens 234 for presbiopia or correction of cataracts is illustrated in FIGS. 44 and 45. This procedure is similar to the previous one but without lenticule removal. Non-invasive lens modification is performed by laser pulse cuts at area 451. In particular, the procedure is one in which lens 234 has developed areas that are becoming opaque to light. The laser beam pulses are tailored temporally and in terms of their intensity to achieve a local modification of the tissue that renders it more transparent and less opaque to light. This type of procedure can delay or even mitigate the need for lens replacement through a cataract surgery. The advantage of the present system is that NLO imaging can optionally be used to determine the regions that need the treatment. The temporal pulse shaper can also be used to determine the optimum laser parameters to maximize the bleaching while preventing thermal damage or the formation of bubbles. It is also desirable to maintain the laser intensity well below the damage limits that may cause retinal damage. The high repetition rate makes the process very fast. The software and surgical steps may be conducted in an automated manner using computer control or manually by the user.

Figure 39:
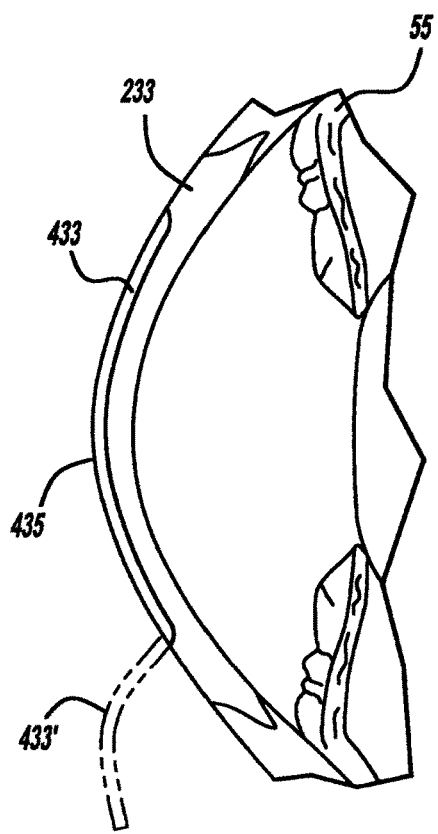
FIG. 39 is a sectional view showing flap creation used with the laser system.
Figure 40:
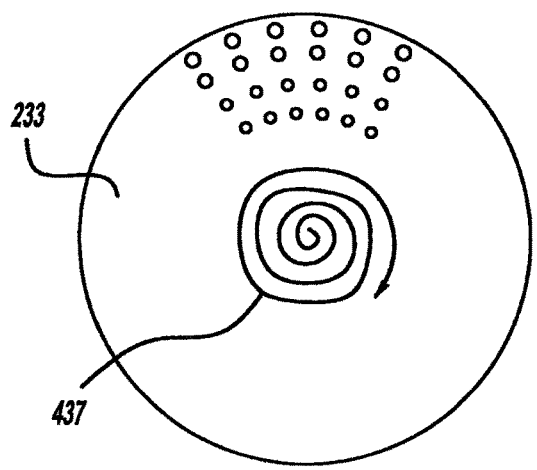
FIG. 40 is a true elevational view showing a cornea flap cutting pattern used with the laser system.

Referring to FIGS. 39 and 40, another application of the present laser system is in the cutting of a flap 433 on a layer of cornea 233 that can then be retracted or folded back in order to perform refractive correction. Refractive correction can then take place using femtosecond laser 53 or with an additional UV laser, preferably one with a wavelength of less than 193 nm (although all of the advantages may not be achieved). Once the refractive correction is performed, flap 433 is returned to its original place. For this use, the laser focus is scanned while remaining at a constant depth from an epithelium 435 designated by the doctor, typically between 100-150 microns in depth. Given the natural eye curvature, it is important to track the depth of eye 55 by smooth adjustment of the z-axis during the cutting of the flap. In these cases, a spiral pattern 437 for ablation is advantageous because it is least demanding on the z axis adjustment.

FIG. 41 shows regular line pattern which creates dispersive grating like behavior with traditional refractive correction cuts. Eye procedures use a femtosecond-laser to ablate a region of the eye, such as the creation of a flap for LASIK. In these cases, a cut is made that is typically between 100 and 150 microns inside the stroma. The laser is scanned in a spiral or raster scan pattern. A variable scanning rate controls the desired pulse-to-pulse overlap. For pulses less than 100 fs, it is desirable to achieve an overlap from one pulse to a subsequent pulse from 0.1% to 50%, and more preferably 5-20%, based on the movement speed of the mirror mounted on galvanometers 400, the diameter of the focal spot, and the repetition rate. The raster scan method is better because it leads to very even laser spot density, however, the creation of regular line patterns in the eye leads to the creation of grating-like patterns that disperse light. With conventional straight row raster patterns, patients report the vision of rainbows when they see lights in the night.

In contrast, the solution to this problem as presented with the present system is to introduce a small amplitude and fast oscillation in the x and y scanners in order to create disorder in the raster scan. This is illustrated in FIG. 42. The overlap between subsequent laser pulses is minimized and the speed of the laser processing is maximized. The present system causes laser beam pulse cuts 441 in a back and forth, row by row manner, while simultaneously oscillating one of the x and y scanner mirror movements (through computer control of the galvonometer 400 actuating the mirrors) by a fraction of the inter-line distance to create sufficient disorder. Repetition rate proposed is greater than 2 MHz which creates smoother cuts. The slow moving mirror has minor oscillations to deter the rows from being perfectly straight. Having a faster repetition rate laser will allow faster scanning and cause the ablation points to be closer together. The pulse duration is preferably less than 150 fs, more preferably less than 100 fs, and most preferably less than 10 fs.

FIGS. 43a and b disclose the use of a pulse shaper that is located between the laser and the eye that is capable of shaping the temporal shape of the pulse. One of the simplest manipulations is to deliver the shortest duration pulses. The shortest pulses have the highest peak intensity and lead to the greatest efficiency. For example, with all of the embodiments and uses of the present system, the use of very short pulses with duration of 50 fs or less is able to exceed the ablation threshold but minimize the total energy of the laser that enters the eye. It is possible with such lasers to use from 10 to 50 times less laser energy than is traditionally being used. The low energy pulses are thereby able to perform with much greater spatial precision, cause less collateral damage, generate little or no gas bubbles and result in better outcomes. Active pulse compression, through dispersion precompensation, optimizes the pulses so that they achieve their maximum peak intensity at the focal spot. Temporal shaping can also be used to create pulse trains, and to create special temporal patterns such as a fast rise followed by a slow decay. Such pulses are advantageous in that they quickly generate free electrons that are then accelerated by the lower intensity but longer lived part of the pulse. Finally, pulses can be generated that have lower intensity and are ideal for NLO imaging but are kept below the ablation threshold. These and many other temporal shapes can be achieved by the pulse shaper.

While various embodiments have been disclosed, it should be appreciated that additional modifications can be made. For example, a prism, grism, parabolic mirror and/or concave mirror can replace the diffracting and collimating optics. Additionally, the pulse shaper can be an SLM, deformable mirror, or an acusto optic programmable dispersive filter. Nevertheless, such changes, modifications or variations are not to be regarded as a departure from the spirit and scope of the invention.

The invention claimed is:

1. An ophthalmic surgical laser system comprising:
an ophthalmic laser emitting at least one unamplified laser pulse, each having a duration less than 150 fs with an output less than 2 µJ and a repetition rate greater than 0.5 MHz, the ophthalmic laser being one of: a direct diode pumped laser, and a Yb doped gain medium laser;
at least one optic changing a characteristic of the pulse between the ophthalmic laser and a target focal point;
the at least one optic further comprising at least one of:

(a) a pulse shaper which assists in correcting nonlinear spectral phase distortions in the pulse to reduce undesired bubbles otherwise created by surgical ophthalmical use of the pulse; and (b) a diffraction optic for diffracting colors in the pulse, a collimating optic for collimating the colors in the pulse and a focusing optic focusing the colors in the pulse at the target focal point at a desired spectral focusing depth;

a programmable controller;

a detector connected to the programmable controller;

the at least one laser pulse scanning across a portion of an eye by a scanner and the detector collecting a nonlinear optical signal based on the laser pulse scan; and the laser, detector and controller causing nonlinear optical imaging of the portion of the eye, instead of using optical coherent tomography, to create a three dimensional map to assist in guiding subsequent eye surgery tailored to the that specific eye using subsequent laser pulses.

2. The laser system of claim 1, wherein the at least one optic is the diffraction, collimating and focusing optics, the diffraction optic is a grating and focusing optic is a curved mirror, further comprising a computer controlled actuator operably moving the mirror to vary the desired spectral focusing depth.

3. The laser system of claim 1, further comprising an objective lens for focusing the pulse at the target focal point to create an indicating ophthalmic mark to aid in at least one of focusing and calibration during a subsequent ophthalmic procedure.

4. The laser system of claim 1, further comprising a portion of an eye is cut by the pulse, the target focal point being located in or on the eye.

5. The laser system of claim 1, wherein the ophthalmic laser is adapted to act on an eye for at least three operations selected from the following: refractive correction, cutting corneal flaps, treatment of macular degeneration, corneal grafting, phaco chopping, lens extraction, photo bleaching, presbiopia correction, and fundus imaging.

6. The laser system of claim 1, further comprising at least a second ophthalmic laser emitting at least one unamplified laser pulse, each of the lasers having a duration less than 80 fs with an output less than 0.5 µJ and a repetition rate greater than 5 MHz, the lasers being of a modularized construction and mounted to a single ophthalmic surgical machine such that laser emission can be easily interchanged for one another almost instantaneously.

7. The laser system of claim 1, further comprising a programmable controller using software which automatically measures nonlinear optical distortions in the laser pulse in less than one minute and compresses the pulses by pre-compensating dispersion.

8. The laser system of claim 1, wherein the target focal point coincides with an eye lens which is cut in a contiguous pattern by the at least one laser pulse such that the eye lens is removable as a single piece and replaced by an intraocular lens.

9. The laser system of claim 1, further comprising a nonlinear polarizer providing mode locking, and an intracavity spectral filter being associated with the laser.

10. The laser system of claim 1, further comprising a compact free space oscillator producing pulses longer than 100 fs, followed by a fiber whose self-phase modulation causes sufficient bandwidth to compress the pulses to durations shorter than 50 fs.

11. The laser system of claim 1, wherein the at least one optic includes a pulse shaper which causes each of the pulses to separate into a train of at least two pulses.

12. The laser system of claim 1, wherein the at least one optic further comprises an objective lens having an aperture that is operable to limit a numerical aperture in order to change a length over which the laser alters tissue of an eye.

13. The laser system of claim 1, wherein the laser is a sub-30 fs titanium:sapphire laser with a repetition rate greater than 1 MHz and a pulse energy less than 20 nJ.

14. The laser system of claim 1, wherein a portion of the at least one pulse is reflected to a set of optics that replicates a dispersion of an objective, eye piece and eye, and provides real-time information about a quality of the at least one pulse being delivered to the eye.

15. The laser system of claim 1, wherein the at least one pulse is transmitted through epithelial cells to selectively image and/or treat different layers of a macula lutea or ganglion cells.

16. An ophthalmic surgical laser system comprising:

an ophthalmic laser emitting at least one unamplified laser pulse, each having a duration less than 150 fs with an output less than 2 µJ and a repetition rate greater than 0.5 MHz, the ophthalmic laser being one of: a direct diode pumped laser, and a Yb doped gain medium laser;

at least one pulse shaper changing a characteristic of the pulse between the ophthalmic laser and a target focal point, the pulse shaper assisting in correcting nonlinear spectral phase distortions in the pulse to reduce undesired bubbles otherwise created by surgical ophthalmical use of the pulse, the pulse shaper controlling amplitude and phase characteristics of the pulse; and a programmable controller varying the pulse shaper in an automated and real-time manner to optimize desired performance through varying a temporal characteristic of the pulse.

17. The laser system of claim 16, further comprising:

a detector connected to the programmable controller;

the at least one laser pulse scanning across a portion of an eye and the detector collecting a nonlinear optical signal based on the laser pulse scan; and the laser, detector and controller causing nonlinear optical imaging of the portion of the eye, instead of using optical coherent tomography, to create a three dimensional map to assist in guiding subsequent eye surgery tailored to the eye using subsequent laser pulses.

18. The laser system of claim 16, further comprising an objective lens for focusing the pulse at the target focal point to create an indicating ophthalmic mark to aid in at least one of focusing and calibration during a subsequent ophthalmic procedure.

19. The laser system of claim 16, further comprising a portion of an eye is cut by the pulse, the target focal point being located in or on the eye.

20. The laser system of claim 16, wherein the ophthalmic laser is adapted to act on an eye for at least three operations selected from the following: refractive correction, cutting corneal flaps, treatment of macular degeneration, corneal grafting, phaco chopping, lens extraction, photo bleaching, presbiopia correction, and fundus imaging.

21. The laser system of claim 16, wherein the programmable controller uses software to automatically measure nonlinear optical distortions in the laser pulse in less than one minute and compress the pulses by pre-compensating dispersion.

22. An ophthalmic surgical laser system comprising:
an ophthalmic laser emitting at least one unamplified laser pulse, each having a duration less than 150 fs with an output less than 2 µJ and a repetition rate greater than 0.5 MHz, the ophthalmic laser being one of: a direct diode pumped laser, and a Yb doped gain medium laser; and
at least one optic changing a characteristic of the pulse between the ophthalmic laser and a target focal point;
the at least one optic further comprising at least one of:
(a) a pulse shaper which assists in correcting nonlinear spectral phase distortions in the pulse to reduce undesired bubbles otherwise created by surgical ophthalmical use of the pulse; and
(b) a diffraction optic for diffracting colors in the pulse, a collimating optic for collimating the colors in the pulse and a focusing optic focusing the colors in the pulse at the target focal point at a desired spectral focusing depth;
wherein fiber and a free space oscillator are combined to generate a laser pulse bandwidth greater than 60 nm.

23. An ophthalmic surgical laser system comprising:
an ophthalmic laser emitting at least one unamplified laser pulse, each having a duration less than 150 fs with an output less than 2 µJ and a repetition rate greater than 0.5 MHz, the ophthalmic laser being one of: a direct diode pumped laser, and a Yb doped gain medium laser;
at least one optic changing a characteristic of the pulse between the ophthalmic laser and a target focal point;
the at least one optic further comprising at least one of:
(a) a pulse shaper which assists in correcting nonlinear spectral phase distortions in the pulse to reduce undesired bubbles otherwise created by surgical ophthalmical use of the pulse; and
(b) a diffraction optic for diffracting colors in the pulse, a collimating optic for collimating the colors in the pulse and a focusing optic focusing the colors in the pulse at the target focal point at a desired spectral focusing depth; and
gold nanoparticles adapted for location in or on an eye, and the at least one pulse being emitted at the gold nanoparticles to assist in an ophthalmic surgery.

24. An ophthalmic surgical laser system comprising:
an ophthalmic laser emitting at least one laser pulse, each having a duration less than 150 fs;
a diffracting optic operably diffracting colors in the pulse;
a collimating optic operably collimating the colors in the pulse;
a focusing optic focusing the colors in the pulse at a target focal point; and
a programmable controller operably causing the target focal point to be at a desired spectral focusing eye depth to allow for laser eye surgery at the desired spectral focusing eye depth but without affecting the adjacent areas subject to the unfocused laser pulse;
wherein the optics and controller cause all of the frequencies of the laser pulse to overlap in space and time at the target focal point while maximum peak intensity is achieved.

25. The laser system of claim 24, wherein the diffracting optic is a grating, the collimating optic is another grating and the focusing optic is an objective lens.

26. The laser system of claim 24, further comprising a detector connected to the controller operably receiving laser induced non-linear signals from a position of the laser focus in order to create a three dimensional map of a portion of an eye acted upon by the scanning laser pulse, the controller using the three dimensional map to assist in determining the subsequent target focal point for eye surgery.

27. The laser system of claim 24, further comprising an actuator controlled by the controller in order to cause the focusing optic to change a location of the target focal point.

28. The laser system of claim 24, wherein the target focal point is adjacent an eye retina to allow for laser treatment at a desired depth with minimal damage to adjacent tissues.

29. The laser system of claim 24, further comprising an objective lens having an aperture that is operable to limit a numerical aperture in order to change a length over which the laser alters tissue of the eye.

30. The laser system of claim 24, wherein the target focal point is at an intraocular lens, and the at least one pulse modifies stiffness of an arm extending from the intraocular lens to adjust its position in the eye.

31. The laser system of claim 24, wherein the target focal point in at an intraocular lens, and the at least one pulse alters a refractive characteristic of the intraocular lens through multi-photon excitation.

32. The laser system of claim 24, wherein the target focal point is within a stroma and the at least one pulse alters a refractive characteristic of an intraocular lens through multi-photon excitation.

33. The laser system of claim 24, wherein the target focal point is within a stroma of the eye and the laser changes a refractive characteristic in order to affect overall optical focusing properties of a cornea of the eye to achieve refractive correction without cutting.

34. The laser system of claim 24, wherein the target focal point is within an artificial intraocular lens and the laser changes a refractive characteristic in order to fine tune an overall optical focusing property of the intraocular lens to achieve refractive correction without surgery.

35. The laser system of claim 1, further comprising a second harmonic generation optic, a second harmonic generation spectrum is obtained when the laser is focused on the second harmonic generation optic to provide information about the pulse duration and peak intensity of the pulse.

36. The laser system of claim 1, wherein the laser output is less than 0.5 µJ.

37. An ophthalmic surgical laser system comprising:
an ophthalmic laser emitting at least one laser pulse, each having a duration less than 150 fs;
a diffracting optic operably diffracting colors in the pulse;
a collimating optic operably collimating the colors in the pulse;
a focusing optic focusing the colors in the pulse at a target focal point;
a programmable controller operably causing the target focal point to be at a desired spectral focusing eye depth to allow for laser eye surgery at the desired spectral focusing eye depth but without affecting the adjacent areas subject to the unfocused laser pulse;
the controller adjusting intensity of diodes pumping the laser; and
an attenuator controlling bandwidth and output intensity of the laser.

38. The laser system of claim 37, wherein the optics and controller cause all of the frequencies of the laser pulse to overlap in space and time at the target focal point while maximum peak intensity is achieved.

39. An ophthalmic surgical laser system comprising:
an ophthalmic laser emitting at least one laser pulse, each having a duration less than 150 fs;
a programmable controller connected to the laser; and a detector connected to the controller, the detector operably detecting at least one of: (a) second harmonic generation imaging; and (b) at least two-photon fluorescence emission imaging, caused by the laser pulse being emitted into an eye;

the controller operably determining at least one of: (i) measurements, (ii) locations, and (iii) characteristics, of portions of the eye based on the detected images, used in subsequent laser treatment of the eye;

wherein the detector and controller detect an image of an iris of the eye and automatically compare a detected image to a previously stored iris image in order to identify the eye being treated and assist with alignment.

40. The laser system of claim 39, wherein the detector detects multi-photon fluorescence emission, and the pulse duration is less than 100 fs.

41. The laser system of claim 39, wherein the detector detects second harmonic generation emission, and the pulse duration is less than 100 fs.

42. The laser system of claim 39, further comprising a pulse shaper connected to the controller, the controller automatically varying the pulse shaper in real time based on required depth to provide optimal dispersion pre-compensation.

43. An ophthalmic surgical laser system comprising:
an ophthalmic laser emitting at least one laser pulse, each having a duration less than 150 fs;
a programmable controller connected to the laser;
a detector connected to the controller, the detector operably detecting at least one of: (a) second harmonic generation imaging; and (b) at least two-photon fluorescence emission imaging, caused by the laser pulse being emitted into an eye;
the controller operably determining at least one of: (i) measurements, (ii) locations, and (iii) characteristics, of portions of the eye based on the detected images, used in subsequent laser treatment of the eye; and
a pulse shaper connected to the controller, the controller automatically varying the pulse shaper in a real time manner to change a characteristic of the at least one pulse.

44. The laser system of claim 43, wherein the detector and controller detect an image of an iris of the eye and automatically compare a detected image to a previously stored iris image in order to identify the eye being treated and assist with alignment.

45. An ophthalmic surgical laser system comprising:
a first ophthalmic laser emitting at least one unamplified laser pulse, each having a duration less than 150 fs with an output less than 2 µJ and a repetition rate greater than 0.5 MHz;
at least one optic changing a characteristic of the pulse between the ophthalmic laser and a target focal point;
the at least one optic further comprising at least one of:
(a) a pulse shaper which assists in correcting nonlinear spectral phase distortions in the pulse to reduce undesired bubbles otherwise created by surgical ophthalmical use of the pulse; and
(b) a diffraction optic for diffracting colors in the pulse, a collimating optic for collimating the colors in the pulse and a focusing optic focusing the colors in the pulse at the target focal point at a desired spectral focusing depth; and
at least a second ophthalmic laser emitting at least one unamplified laser pulse, the lasers being of a modularized construction and mounted to a single ophthalmic surgical machine such that laser emission can be easily interchanged for one another almost instantaneously.

46. The laser system of claim 45, wherein the optic is the pulse shaper, further comprising a programmable controller varying the pulse shaper in an automated and real-time manner to optimize desired performance through varying a temporal characteristic of the pulse.

47. The laser system of claim 45, wherein the at least one optic is the diffraction, collimating and focusing optics, the diffraction optic is a grating and focusing optic is a curved mirror, further comprising a computer controlled actuator operably moving the mirror to vary the desired spectral focusing depth.

48. The laser system of claim 45, wherein the ophthalmic laser is adapted to act for at least three different operations selected from the following: refractive correction, cutting corneal flaps, treatment of macular degeneration, corneal grafting, phaco chopping, lens extraction, photo bleaching, presbiopia correction, and fundus imaging.

49. The laser system of claim 45, wherein a fiber and a free space oscillator are combined to generate a laser pulse bandwidth greater than 60 nm.

50. The laser system of claim 45, further comprising a compact free space oscillator producing pulses longer than 100 fs, followed by a fiber whose self-phase modulation causes sufficient bandwidth to compress the pulses.

51. The laser system of claim 45, wherein the pulse from at least one of the lasers provides a high resolution image of a retina of a patient at different depths in order to provide comprehensive health diagnosis based on vasculature and/or on the relative composition of metabolic compounds.

52. The laser system of claim 45, wherein the pulse from at least one of the lasers provides a high resolution image of an endothelium of the patent to determine eye health of a patient.

53. The laser system of claim 45, wherein the pulse from at least one of the lasers activates nanoparticles in an eye of the patient to treat an eye.

54. The laser system of claim 45, wherein the target focal point is at an intraocular lens, and the at least one pulse modifies stiffness of an arm extending from the intraocular lens to adjust its position in an eye.

55. The laser system of claim 45, wherein the target focal point in at an intraocular lens, and the at least one pulse alters a refractive characteristic of the intraocular lens through multi-photon excitation.

56. An ophthalmic surgical laser system comprising:
an ophthalmic laser emitting at least one unamplified laser pulse, each having a duration less than 150 fs with an output less than 2 µJ and a repetition rate greater than 0.5 MHz;
at least one optic changing a characteristic of the pulse between the ophthalmic laser and a target focal point;
the at least one optic further comprising a diffraction optic for diffracting colors in the pulse, a collimating optic for collimating the colors in the pulse and a focusing optic focusing the colors in the pulse at the target focal point at a desired spectral focusing depth;
the diffraction optic being a grating and the focusing optic being a curved mirror; and
a computer controlled actuator operably moving the mirror to vary the desired spectral focusing depth;
the ophthalmic laser being adapted for at least three different eye operations selected from the following: refractive correction, cutting corneal flaps, treatment of macular degeneration, corneal grafting, phaco chopping, lens extraction, photo bleaching, presbiopia correction, and fundus imaging.

57. The laser system of claim 56, further comprising:
a programmable controller connected to the laser; and
a detector connected to the controller, the detector operably detecting at least one of: (a) second harmonic generation imaging; and (b) at least two-photon fluorescence emission imaging, caused by the laser pulse being emitted into the eye;
the controller operably determining at least one of: (i) measurements, (ii) locations, and (iii) characteristics, of portions of the eye based on the detected images, used in subsequent laser treatment of the eye.

58. The laser system of claim 57, wherein the detector detects multi-photon fluorescence emission, and the pulse duration is less than 100 fs.

59. The laser system of claim 57, wherein the detector detects second harmonic generation emission, and the pulse duration is less than 100 fs.

60. The laser system of claim 56, further comprising a programmable controller using software which automatically measures nonlinear optical distortions in the laser pulse in less than one minute and compresses the pulses by pre-compensating dispersion.

61. The laser system of claim 56, wherein fiber and free space elements are combined to generate a laser pulse bandwidth greater than 60 nm.

62. The laser system of claim 56, wherein the laser is a titanium:sapphire laser with a repetition rate greater than 1 MHz and a pulse energy less than 20 nJ.

63. The laser system of claim 56, wherein pulses from the laser provide a high resolution image of at least one of: (a) a retina or (b) an endothelium, at different depths of the eye.

64. An ophthalmic surgical laser system comprising:
an ophthalmic laser emitting at least one unamplified laser pulse, each having a duration less than 150 fs with an output less than 2 µJ and a repetition rate greater than 0.5 MHz;
at least one optic changing a characteristic of the pulse between the ophthalmic laser and a target focal point;
the at least one optic further comprising a pulse shaper which assists in correcting nonlinear spectral phase distortions in the pulse to reduce undesired bubbles otherwise created by surgical ophthalmical use of the pulse; and
a programmable controller varying the pulse shaper in an automated and real-time manner to optimize desired performance through varying a temporal characteristic of the pulse;
the ophthalmic laser being adapted for at least three different eye operations selected from the following: refractive correction, cutting corneal flaps, treatment of macular degeneration, corneal grafting, phaco chopping, lens extraction, photo bleaching, presbiopia correction, and fundus imaging.

65. The laser system of claim 64, wherein the programmable controller uses software which automatically measures nonlinear optical distortions in the laser pulse in less than one minute and compresses the pulses by pre-compensating dispersion.

66. The laser system of claim 64, wherein fiber and free space elements are combined to generate a laser pulse bandwidth greater than 60 nm.

* * * * *